United States Patent
Li

(10) Patent No.: US 10,596,218 B2
(45) Date of Patent: *Mar. 24, 2020

(54) COIX SEED OIL CONTAINING 16 GLYCERIDES, AND PHARMACEUTICAL PREPARATION AND USE THEREOF

(71) Applicant: ZHEJIANG KANGLAITE GROUP CO., LTD., Hangzhou, Zhejiang (CN)

(72) Inventor: Dapeng Li, Zhejiang (CN)

(73) Assignee: ZHEJIANG KANGLAITE GROUP CO., LTD., Hangzhou, Zhejiang (CN)

( * ) Notice: Subject to any disclaimer, the term of this patent is extended or adjusted under 35 U.S.C. 154(b) by 315 days.

This patent is subject to a terminal disclaimer.

(21) Appl. No.: 15/324,890

(22) PCT Filed: Jul. 17, 2015

(86) PCT No.: PCT/CN2015/084298
§ 371 (c)(1),
(2) Date: Jan. 9, 2017

(87) PCT Pub. No.: WO2016/008443
PCT Pub. Date: Jan. 21, 2016

(65) Prior Publication Data
US 2017/0209518 A1 Jul. 27, 2017

(30) Foreign Application Priority Data
Jul. 18, 2014 (CN) .......................... 2014 1 0342420

(51) Int. Cl.
| | | |
|---|---|---|
| *A61K 36/8994* | (2006.01) |
| *A61K 9/10* | (2006.01) |
| *A61K 9/48* | (2006.01) |
| *A61K 9/14* | (2006.01) |
| *A61K 9/08* | (2006.01) |
| *A61K 31/21* | (2006.01) |
| *A61K 9/20* | (2006.01) |
| *A61K 9/127* | (2006.01) |
| *A61K 9/00* | (2006.01) |
| *A61K 31/231* | (2006.01) |
| *A61K 31/232* | (2006.01) |
| *A61K 47/10* | (2017.01) |
| *A61K 47/24* | (2006.01) |

(52) U.S. Cl.
CPC ........ *A61K 36/8994* (2013.01); *A61K 9/0019* (2013.01); *A61K 9/08* (2013.01); *A61K 9/10* (2013.01); *A61K 9/127* (2013.01); *A61K 9/14* (2013.01); *A61K 9/20* (2013.01); *A61K 9/48* (2013.01); *A61K 9/4833* (2013.01); *A61K 9/4858* (2013.01); *A61K 9/4866* (2013.01); *A61K 31/21* (2013.01); *A61K 31/231* (2013.01); *A61K 31/232* (2013.01); *A61K 47/10* (2013.01); *A61K 47/24* (2013.01); *A61K 2236/15* (2013.01); *A61K 2236/37* (2013.01); *A61K 2236/55* (2013.01)

(58) Field of Classification Search
None
See application file for complete search history.

(56) References Cited

U.S. PATENT DOCUMENTS

2014/0370129 A1 12/2014 Li

FOREIGN PATENT DOCUMENTS

| CN | 1080176 A | 1/1994 |
| CN | 1485072 A | 3/2004 |
| CN | 1485418 A | 3/2004 |
| CN | 104173824 A | 12/2014 |

OTHER PUBLICATIONS

Xiang, Zhimin et al., "Identification of Triacylglycerols in Coix Oil by High Performance Liquid Chromatography-Atmospheric Pressure Chemicalionization-Mass Spectrometry", China Journal of Chinese Materia Medica, vol. 33, No. 18, Sep. 30, 2005 (Sep. 30, 2005), pp. 1436-1438.

*Primary Examiner* — Terry A McKelvey
*Assistant Examiner* — Catheryne Chen
(74) *Attorney, Agent, or Firm* — Global IP Services; Tianhua Gu

(57) ABSTRACT

The present invention relates to *Coix* seed oil extracted from Semen Coicis, pharmaceutical preparations thereof, and the use thereof in the treatment of tumors. Specifically, the *Coix* seed oil contains 5 diglyceride and 11 triglyceride ingredients in the following mass percentages: 1,3-diolein 0.40-0.58%, 1-linolein-3-olein 0.91-1.31%, 1,2-diolein 0.24-0.35%, 1-olein-2-linolein 0.66-0.95%, 1,2-dilinolein 0.33-0.47%, trilinolein 4.87-6.99%, 1-olein-2,3-dilinolein 13.00-18.69%, 1-palmitin-2,3-dilinolein 5.25-7.54%, 1,3-diolein-2-linolein 13.23-19.02%, 1-palmitin-2-linolein-3-olein 10.26-14.75%, 1,3-dipalmitin-2-linolein 2.28-3.28%, triolein 14.44-20.76%, 1-palmitin-2,3-diolein 8.06-11.58%, 1-olein-2-linolein-3-stearin 1.37-1.97%, 1,3-dipalmitin-2-olein 1.52-2.19% and 1,2-diolein-3-stearin 1.29-1.86%.

6 Claims, No Drawings

COIX SEED OIL CONTAINING 16 GLYCERIDES, AND PHARMACEUTICAL PREPARATION AND USE THEREOF

CROSS REFERENCE TO RELATED PATENT APPLICATION

The present application is the US national stage of PCT/CN2015/084298 filed on Jul. 17, 2015, which claims the priority of the Chinese patent application No. 201410342420.8 filed on Jul. 18, 2014, which applications are incorporated herein by reference.

FIELD OF THE INVENTION

The present invention relates to the pharmaceutical field, specifically, the present invention relates to *Coix* seed oil, pharmaceutical preparations thereof, the process for the preparation of same and the use thereof in the preparation of antitumor drugs.

BACKGROUND OF THE INVENTION

*Coix* seeds are dried ripe seeds of *Coix lacryma-jobi* L. var *ma-yuen* (Roman.), Stapf, a genus of plant in the Poaceae family. It is a dampness-eliminating drug and has been used as a medicinal and edible plant for a long time. Modern researches have found that *Coix* seeds have many pharmacological effects, such as analgesic anti-inflammatory, immunomodulatory, anti-ulcer, hypolipidemic and anti-obesity effects. In recent years, researchers around the world have studied the chemical composition of the *Coix* seed by using TLC, HPLC-MS, GC, etc., and found a variety of active ingredients in it, including coixenolide, triglycerides, fatty acids, lactams, *Coix* lactones, saccharides, sterols and triterpenoids. Among them, esters are the first discovered components having anti-tumor activities and the most reported chemical composition attracting the most attention. Kanglaite injection, in which the active ingredient is *Coix* seed oil, has been widely used in present Chinese clinical applications, but the *Coix* seed oil used in the Kanglaite injection comprises complex components. In addition to triglycerides, it also contains monoglycerides, diglycerides and fatty acid esters, etc. This will inevitably be a great challenge for the quality control in the practical production process and the safety in clinical applications.

In the present invention, the raw material *Coix* seed powder has been treated by supercritical carbon dioxide extraction, basification, neutral alumina purification and kaolin purification, etc., to afford an effective part, *Coix* seed oil. With the active ingredients' isolation and identification, it is determined that the *Coix* seed oil comprises mainly 11 triglyceride components and 5 diglyceride components. Further determination of its physicochemical constants has confirmed the optimal acid value, iodine value, saponification value, refractive index and specific gravity, etc. The use of the *Coix* seed oil of the invention in medication has advantages such as the confirmed composition of ingredients, ensuring quality stability in every batch in the industrial production, and avoiding toxic and side effects brought about by the complex ingredients while adopting *Coix* seed oil directly.

SUMMARY OF THE INVENTION

The first aspect of the invention is to provide a *Coix* seed oil extracted from Semen Coicis. The *Coix* seed oil contains 5 diglyceride and 11 triglyceride ingredients in the following mass percentages: 1,3-diolein 0.40-0.58%, 1-linolein-3-olein 0.91-1.31%, 1,2-diolein 0.24-0.35%, 1-olein-2-linolein 0.66-0.95%, 1,2-dilinolein 0.33-0.47%, trilinolein 4.87-6.99%, 1-olein-2,3-dilinolein 13.00-18.69%, 1-palmitin-2,3-dilinolein 5.25-7.54%, 1,3-diolein-2-linolein 13.23-19.02%, 1-palmitin-2-linolein-3-olein 10.26-14.75%, 1,3-dipalmitin-2-linolein 2.28-3.28%, triolein 14.44-20.76%, 1-palmitin-2,3-diolein 8.06-11.58%, 1-olein-2-linolein-3-stearin 1.37-1.97%, 1,3-dipalmitin-2-olein 1.52-2.19% and 1,2-diolein-3-stearin 1.29-1.86%.

Preferably, mass percentage contents of the above 5 diglyceride and 11 triglyceride ingredients are: 1,3-diolein 0.45-0.55%, 1-linolein-3-olein 1.03-1.25%, 1,2-diolein 0.27-0.33%, 1-olein-2-linolein 0.75-0.91%, 1,2-dilinolein 0.37-0.45%, trilinolein 5.47-6.69%, 1-olein-2,3-dilinolein 14.63-17.88%, 1-palmitin-2,3-dilinolein 5.90-7.21%, 1,3-diolein-2-linolein 14.88-18.19%, 1-palmitin-2-linolein-3-olein 11.55-14.11%, 1,3-dipalmitin-2-linolein 2.57-3.14%, triolein 16.25-19.86%, 1-palmitin-2,3-diolein 9.07-11.08%, 1-olein-2-linolein-3-stearin 1.54-1.88%, 1,3-dipalmitin-2-olein 1.71-2.09% and 1,2-diolein-3-stearin 1.45-1.78%.

More preferably, mass percentage contents of the above 5 diglyceride and 11 triglyceride ingredients are: 1,3-diolein 0.49-0.51%, 1-linolein-3-olein 1.12-1.16%, 1,2-diolein 0.29-0.31%, 1-olein-2-linolein 0.81-0.85%, 1,2-dilinolein 0.40-0.42%, trilinolein 5.96-6.20%, 1-olein-2,3-dilinolein 15.93-16.58%, 1-palmitin-2,3-dilinolein 6.43-6.69%, 1,3-diolein-2-linolein 16.20-16.87%, 1-palmitin-2-linolein-3-olein 12.57-13.09%, 1,3-dipalmitin-2-linolein 2.79-2.91%, triolein 17.69-18.42%, 1-palmitin-2,3-diolein 9.87-10.27%, 1-olein-2-linolein-3-stearin 1.68-1.74%, 1,3-dipalmitin-2-olein 1.86-1.94% and 1,2-diolein-3-stearin 1.58-1.65%.

The above contents refer to the mass percentage contents of diglyceride and triglyceride compounds in the *Coix* seed oil. 5 diglyceride and 11 triglyceride monomer compounds can be separated by using preparative chromatography from the *Coix* seed oil prepared by the following steps, and their contents can be obtained by weighing and calculating the products. They can also be obtained according to conventional analytic methods in the art.

The *Coix* seed oil has the following physicochemical constants based on the fatty oils: specific gravity at 20° C. 0.916-0.920, refractive index at 20° C. 1.471-1.474, acid value<0.2, iodine value 100-106, saponification value 186-195.

The *Coix* seed oil of the invention can be prepared by a process comprising steps of:

(1) Supercritical carbon dioxide extraction:

Crushing *Coix* seeds into 20-100 mesh powder and extracting the powder using a supercritical $CO_2$ extraction system in which *Coix* seed powder is put in 600 L×2 extractors; the $CO_2$ preheater, extractor and separation column are heated by jacketed circulating hot water to make the extraction temperature and separation temperature to be 33-45° C. and 30-45° C., respectively; the outlet temperatures of separator I and separator II are kept at 20-50° C. and 15-35° C., respectively; the liquid $CO_2$ is pressed at a flow rate of 1-3 t/h into the $CO_2$ preheater via a high pressure pump, turning into a fluid in supercritical state; in the extractor, an oil is extracted into the $CO_2$ fluid at a pressure of 19-23 Mpa; then the $CO_2$ fluid with this oil enters the separation column in which the pressure is controlled to 7-10 Mpa to separate this oil; the $CO_2$ gas out from the separation column enters sequentially into separator I and separator II in which the pressure is sustained at 5-7 Mpa and 4-6 Mpa, respectively; impurities such as water separated therefrom are discarded; the $CO_2$ gas returns to liquid $CO_2$ for reuse through a condenser; and a continuous extraction for 2-3 h affords a crude *Coix* seed oil; and (2) refining process:

adding 65% petroleum ether (bp. 60° C.–90° C.), based on the oil weight, into the *Coix* seed oil obtained by the supercritical $CO_2$ extraction; adding 2% NaOH aqueous solution in an amount ranging from 36% to 56% of the oil weight according to the acid value; after stirring the mixture for 10 min and standing for 18-24 h, removing the lower niger layer; washing the upper layer with purified water and letting standing for 18-24 h; after the removal of the lower waste water, washing the upper layer again; after standing for another 40-50 h, removing the lower waste water; and demulsifying the upper layer with acetone in an amount of 70%-90% of the oil weight; after standing for 2-4 h, removing the lower waste acetone and adding 3% to 8% of activated neutral alumina by weight of crude oil in the upper oil layer; stirring the mixture for 30 min, then filtering off the precipitation; heating the filtrate and adding 2% to 6% of activated mixed adsorbent by weight of crude oil; stirring the mixture for 30 min at 40-50° C. and then filtering off the precipitation; concentrating the filtrate under a reduced pressure to recover the solvent, then washing again with purified water; after standing for 1-2 h, removing the lower waste water and heating the upper oil layer and vacuum concentrating it in nitrogen atmosphere; then sterilizing the oil via dry heat sterilization under vacuum at 160-170° C. for 1-2 h; after cooling, filtering the oil through a 0.2 μm microporous membrane; then split charging the obtained *Coix* seed oil in 500 mL glass infusion bottles, nitrogenizing and sealing the bottles.

Preferably, the refining process comprises steps of:

adding petroleum ether (bp. 60° C.–90° C.) into the *Coix* seed oil obtained by the supercritical $CO_2$ extraction in an amount of 65% of the oil weight; adding 2% NaOH aqueous solution in an amount ranging from 36% to 56% of the oil weight according to the acid value; after stirring the mixture for 10 min and standing for 20 h, removing the lower niger layer; washing the upper layer with purified water and letting standing for 22 h; after the removal of the lower waste water, washing the upper layer again; after standing for another 46 h, removing the lower waste water; demulsifying the upper layer with acetone in an amount of 70%-90% by weight of the crude oil and standing for 3 h; removing the lower waste acetone and adding 5% of activated neutral alumina by weight of crude oil in the upper oil layer; stirring the mixture for 30 min, then filtering off the precipitation; heating the filtrate, and adding 4% of mixed adsorbent of activated kaolin and activated carbon (1:1); stirring the mixture for 30 min at 40-50° C., and then filtering off the precipitation; concentrating the filtrate under a reduced pressure to recover the solvent, then washing again with purified water; after standing for 1 h, removing the lower waste water; heating the upper oil layer and vacuum concentrating it in nitrogen atmosphere; then sterilizing the concentrated oil via dry heat sterilization under vacuum at 160-170° C. for 2 h; after cooling, filtering the oil through a 0.2 μm microporous membrane; then split charging the obtained *Coix* seed oil in 500 mL glass infusion bottles, nitrogenizing and sealing the bottles.

The *Coix* seed oil of the invention is a yellowish clear liquid with a light odor and a light taste. It is highly soluble in petroleum ether or chloroform, freely soluble in acetone, slightly soluble in ethanol, but insoluble in water.

The *Coix* seed oil prepared based on the above methods was detected according to the method in the appendix of "Pharmacopoeia of the People's Republic of China" (2010 edition) Volume I. Physicochemical constants thereof are: specific gravity at 20° C. 0.916-0.920, refractive index at 20° C. 1.471-1.474, acid value<0.2, iodine value 100-106, saponification value 186-195. The acid value according to the Pharmacopoeia refers to the weight of potassium hydroxide (in milligrams) needed to neutralize free fatty acids contained in 1 gram of fats, fatty oils, or other similar substances. In the quality study of oil products, acid value is an important evaluation. As far as the *Coix* seed oil of the invention, the acid value is less than 0.2. By the optimization of the preparation process such as supercritical extraction parameters and the purification process like basification, *Coix* seed oil was prepared with the following advantages: on the one hand, it has a very low content of free fatty acid impurities, which means a high product quality; on the other hand, it gathers a great amount of active ingredients of diglycerides and triglycerides in high purity, and the types of diglycerides and triglyceride ingredients therein are determinate, and the contents thereof are stable. In addition, other physicochemical constants, such as saponification value, iodine value, etc., measured between batches of samples, had a small range of variation. It further illustrates that the *Coix* seed oil of the invention has a stable quality and a safer clinical use. The preparation method of the invention gives a stable product with a high yield and a low cost. It is suitable for the industrial production in view of the safety and controllability.

The second aspect of the invention is to provide a pharmaceutical preparation containing *Coix* seed oil, specifically, it comprises a therapeutically effective amount of the *Coix* seed oil of the invention and one or more pharmaceutically acceptable carriers.

Pharmaceutically acceptable carriers can be selected from pharmaceutical conventional dilutions, excipients, fillers, emulsifiers, binders, lubricants, absorption accelerators, surfactants, disintegrants, lubricants and antioxidants, if necessary, flavoring agents, sweeteners, preservative and/or coloring agents.

Pharmaceutically acceptable carriers can be selected from one or more in the group consisting of: mannitol, sorbitol, sodium metabisulfite, sodium bisulfite, sodium thiosulfate, cysteine hydrochloride, thioglycolic acid, methionine, soybean lecithin, vitamin C, vitamin E, EDTA disodium, EDTA calcium sodium, monovalent alkali metal carbonate, acetate, phosphate or its aqueous solution, hydrochloric acid, acetic acid, sulfuric acid, phosphoric acid, amino acids, sodium chloride, potassium chloride, sodium lactate, ethylparaben solution, benzoic acid, potassium sorbate, chlorhexidine acetate, xylitol, maltose, glucose, fructose, dextran, glycine, starch, sucrose, lactose, mannitol, silicic derivatives, cellulose and its derivatives, alginates, gelatin, polyvinyl pyrrolidone, glycerin, Tween 80, agar-agar, calcium carbonate, calcium bicarbonate, surfactants, polyethylene glycol, cyclodextrin, β-cyclodextrin, phospholipid material, kaolin, talc, and calcium stearate or magnesium stearate.

The pharmaceutical preparation of the invention can be oral solid preparations, oral liquid preparations or injections.

Preferably, the oral solid preparation is selected from any one of capsules, tablets, dripping pills, granules, and concentrated pills; the oral liquid preparation is selected from any one of aqueous or oily suspensions, solutions, emulsions, syrups or elixirs, and a dry product that may be reconstructed by water or other suitable carrier(s) before use; and the injection is selected from any one of nano suspensions, liposomes, emulsions, lyophilized powder for injection and aqueous injection.

More preferably, the injection comprises the following components: the *Coix* seed oil of the invention 50-350 g, soybean lecithin for injection or soybean lecithin acceptable for injection 10-40 g, glycerin for injection or glycerin acceptable for injection 15-50 g, and Water for injection added to 1000 mL.

The injection of the invention can be prepared by a method comprising steps of:

adding appropriate amount of water for injection to a formulated amount of soybean lecithin for injection or soybean lecithin acceptable for injection; dispersing the mixture with a high shear dispersing emulsifier to give a dispersion without bulks or granules; adding a formulated amount of glycerin for injection or glycerin acceptable for injection; then adding water for injection to a specified amount, and stirring the mixture to give a water phase;

weighing a formulated amount of *Coix* seed oil; heating the weighed oil and the water phase separately to 60-70° C., then mixing them and emulsifying the mixture in a high pressure homogenizer, in which the low pressure is 5-12 MPa and the high pressure is 25-50 MPa; repeating the cycle of homogenization for 3-6 times until the amount of particles below 2 μm is no less than 95% and particles above 5 μm are undetectable; if necessary, using NaOH or HCl to adjust the pH to 4.8 to 8.5, preferably 6.8 to 7.0, most preferably 6.8; and filtering the resulting homogeneous emulsion by nitrogen pressure through a microporous filter of 3 μm or less; filling the emulsion, nitrogenizing, sterilizing and cooling to afford the injection.

The capsule of the invention comprises the following components: *Coix* seed oil 200-800 g, antioxidant(s) and/or emulsifier(s) 0.20-0.60 g for 1000 capsules.

The capsule of the invention can be prepared by a method comprising steps of:

preparing glue solution: weighing gelatin, purified water, glycerin and a preservative at a weight ratio of 1:0.6-1.2:0.3-0.8:0.0001-0.01; adding glycerin, purified water and preservative (selected from any one of 10% ethylparaben solution, benoic acid, potassium sorbate and chlorhexidine acetate) sequentially into a glue melting tank; heating to 70° C.-90° C.; then adding gelatin and constantly stirring the mixture under vacuum until the gelatin is completely dissolved; filtering the glue solution and storing the filtered glue solution at 56-62° C. for use;

preparing drug liquid: adding formulated amount of *Coix* seed oil, antioxidant (Vitamin E) and/or emulsifier (Tween 80) into an dosing tank, and stirring the mixture constantly until being homogeneously mixed; and pressing capsules: choosing proper pellet dies according to the capsule size; pressing capsules in a temperature of 15-30° C. and a relative humidity of less than 35%; drying the pressed and shaped capsules; after removing capsules of abnormal size, washing the normal capsules with 95% medicinal ethanol, and drying them continuously till the moisture content is less than 12%; visually inspecting and removing unqualified capsules; finally printing and packaging to afford the capsules.

It is demonstrated, in pharmacodynamic experiments, that the *Coix* seed oil of the invention and the pharmaceutical preparation thereof have shown different degrees of inhibition on a variety of human tumor cell lines. They can be used as antitumor drugs.

Therefore, another aspect of the invention is to provide a use of the *Coix* seed oil of the invention in the preparation of antitumor drugs.

The tumors refer to lung cancer, liver cancer, pancreatic cancer, prostate cancer, ovarian cancer and breast cancer, in early, middle or late stage.

The following experimental data are used to illustrate anti-tumor effects of the *Coix* seed oil of the invention and the pharmaceutical preparations thereof.

I. Inhibition of *Coix* Seed Oil and Preparations Thereof on 8 Human Tumor Cell Lines in MTT Method In Vitro A. Experimental Materials and the Preparation Thereof:

(1) Cell lines: PANC-1 (human pancreatic cancer cells), SKOV3 (human ovarian cancer cells), MCF-7 (human breast cancer cells), Bcap-37 (human breast cancer cells), SMMC-7721 (human hepatic cancer cells), HepG-2 (human hepatic cancer cells), A549 (human lung cancer cells) and H460 (human lung cancer cells), storaged and passaged maintainably in Research and Evaluation Center for Pharmacology, Shanghai Institute of Pharmaceutical Industry;

(2) DMEM complete medium supplied with 10% newborn calf serum (GIBCO BRL), 1% of penicillin (100 U/mL)+streptomycin (100 μg/mL);

(3) 0.25% trypsin solution, purchased from Invitrogen Corp. and storaged at −20° C.;

(4) Phosphate buffer (PBS): NaCl 8 g, KCl 0.2 g, $Na_2HPO_4$ 1.15 g and $KH_2PO_4$ 0.2 g, dissolved in 1 L double-distilled water and autoclaved at 121° C. for 20 min, then storaged at 4° C.;

(5) MTT (AMRESCO) solution: 5 mg/ml in PBS;

(6) Formazan crystal dissolving solution: SDS 10 g, isobutanol 5 ml and concentrated hydrochloric acid 0.1 ml, dissolved in 100 ml of deionized double distilled water.

B. Experimental Method

The inhibition effects of samples on the above-mentioned cell lines were detected by using MTT method. The specific procedures were as follows:

(1) Cell culture: (a) Storaged cells were taken out from the liquid nitrogen, thawed quickly in a 37° C. water bath, and aseptically transferred into 6 ml of cellular medium in a 10 ml centrifugal tube, centrifuged at 1000 rpm for 5 min. The supernatant was discarded, then the precipitated cells were re-suspended in 5-6 ml cellular media by pipetting and transferred into a flask in a 37° C. incubator for cell culture; (b) Next day, the flask was taken out from the incubator and the used medium was discarded, then the cells were incubated in 5-6 ml fresh medium in the 37° C. incubator; (c) On the third day, the flask was taken out from the incubator and the used medium was discarded, then 2-3 ml of PBS (pH7.4) was added into the flask with rocking for cleaning it and the used PBS was discarded. Such a cellular cleaning step was repeated once again. 3-5 drops of 0.25% trypsin solution were added into the flask with sloshing, thus well-distributed in it. The flask was capped and placed in a 37° C. incubator for about 3 min, and the separation of cells from the flask wall was observed under the microscope. 2 ml of cellular medium was added and cells were separated completely from the flask wall by pipetting, then the cell suspension was transferred into 2 separate clean flasks, each containing 5-6 ml medium. The cell suspension was well-distributed by pipetting, then the flask was placed in a 37° C. incubator. (d) Step (c) was repeated every other day. In the whole cultivation process, adherent cells were not allowed to grow too dense and suspension cells were always maintained at a logarithmic growth stage.

(2) Preparation of the sample and the control: A proper amount of sample of *Coix* seed oil (oil of Job's tears seed) was dissolved in DMSO to obtain a solution in a concentration of 10 mg/ml. This solution was diluted in a gradient dilution with PBS to obtain a set of sample solutions in the concentration of 10 mg/ml, 5000 µg/ml, 2500 µg/ml, 1250 µg/ml, 625 µg/ml and 312.5 µg/ml, respectively.

(3) Each diluted sample solution was added into duplicated wells of a 96 well flat-bottom microplate (10 µl/well). The correspondingly diluted DMSO solutions, as controls, were added into the wells of the microplate.

(4) Cells in a logarithmic growth stage were trypsinized and washed, then re-suspended in the medium containing 10% calf serum. The number of living cells was counted in Trypan blue dye exclusion method and cell suspensions were adjusted into a density of $2 \times 10^5$ cell/ml.

(5) The cell-contained 96 well flat-bottom microplate was placed in a 37° C. incubator and cells were incubated under 5% $CO_2$ for 48 h.

(6) 20 µl of 5 mg/ml MTT solution was added into each well and cells were incubated continuously in the incubator for 3-4 h.

(7) 100 µl of crystal dissolving solution was added into each well and cells were incubated continuously in the incubator overnight, so as to dissolve the resulted formazan crystals sufficiently. Then, the absorbance value was measured at 570 nm for each well.

(8) Based on absorbance values, inhibition rates on the cell growth were calculated for sample groups of various concentrations. The calculation formula was as follows:

(1−mean absorbance of experimental wells/mean absorbance of control wells)×100%

C. Experimental Results

TABLE 1

Inhibition rates of samples in various concentrations on the cell growth in 8 cell lines (%)

| Cell line | Concentration of Sample | | | | | |
|---|---|---|---|---|---|---|
| | 1000 µg/ml | 500 µg/ml | 250 µg/ml | 125 µg/ml | 62.5 µg/ml | 31.25 µg/ml |
| PANC-1 | 75.94 | 51.21 | 27.59 | 2.98 | 0.24 | 0.01 |
| SKOV3 | 98.20 | 91.35 | 54.57 | 28.55 | 1.66 | / |
| MCF-7 | 86.78 | 50.14 | 49.79 | 40.44 | 31.22 | 23.98 |
| Bcap-37 | 65.42 | 38.78 | 26.17 | 1.11 | 0.87 | 0.34 |
| SMMC-7721 | 98.52 | 96.88 | 84.11 | 35.51 | 27.88 | 13.63 |
| HepG-2 | 66.85 | 43.90 | 31.42 | 4.06 | 2.27 | 0.85 |
| A549 | 97.22 | 67.81 | 43.67 | 24.63 | 17.65 | 10.37 |
| H460 | 74.38 | 42.48 | 25.19 | 15.52 | 7.69 | 0.88 |

TABLE 2

$IC_{50}$ values of samples in 8 cell lines in vitro (µg/ml)

| Cell line | Sample | |
|---|---|---|
| | Coix seed oil | Positive control (Taxol) |
| PANC-1 | 495.4 | 0.44 |
| SKOV3 | 253.04 | 0.22 |
| MCF-7 | 195.73 | 0.34 |
| Bcap-37 | 669.1 | 0.28 |
| SMMC-7721 | 104.76 | 0.12 |
| HepG-2 | 590.9 | 0.45 |
| A549 | 192.63 | 0.49 |
| H460 | 497.1 | 0.49 |

D. Conclusion

The Coix seed oil of the invention in various concentrations has shown the inhibition on 8 human tumor cell lines in different degrees.

Further experiments have confirmed that the Coix seed oil of the invention and preparations thereof can also achieve the desired effects described in the above experimental examples.

The following examples further illustrate the invention, but are not construed as a limitation on the invention.

DETAILED DESCRIPTION OF THE PREFERRED EMBODIMENTS

Example 1 Preparation of Coix Seed Oil

Supercritical carbon dioxide extraction: Coix seeds were crushed into 70 mesh powder and extracted using 600 L×2 supercritical $CO_2$ extractors. Coix seed powder was put in an extractor. The $CO_2$ preheater, extractor and separation column were heated by jacketed circulating hot water, so that the extraction temperature and separation temperature reached 40° C. and 45° C., respectively, and the outlet temperatures of separator I and separator II were kept 50° C. and 35° C., respectively. Liquid $CO_2$ was pressed into the $CO_2$ preheater via a high pressure pump at a flow rate of 2 t/h, turning into a fluid in supercritical state. In the extractor, an oil was extracted into the $CO_2$ fluid at a pressure of 20 Mpa. Then the $CO_2$ fluid with this oil entered a separation column, and the pressure of the separation column was controlled to 7 Mpa to separate the oil. The $CO_2$ gas out from the separation column entered sequentially into separator I and separator II, in which the pressure was sustained at 7 Mpa and 6 Mpa, respectively. Impurities like water separated therefrom were discarded. The $CO_2$ gas returned to liquid $CO_2$ for reuse through a condenser. A continuous extraction for 2.5 h afforded a crude Coix seed oil.

Refining: To the crude Coix seed oil obtained by supercritical $CO_2$ extraction was added 65% petroleum ether (60° C.) based on the oil weight. 45% NaOH aqueous solution (2%) based on the oil weight was added according to the acid value. After stirring for 10 min, then standing for 20 h, the lower niger layer was removed. The upper layer was washed with purified water and let stand for 22 h. After the removal of the lower waste water, the upper layer went on a second washing. After standing for another 46 h, the lower waste water was removed, and the upper layer was demulsified by adding 80% acetone based on the oil weight. After standing for 3 h, the lower waste acetone was removed. The upper oil layer was added 5% activated neutral alumina by weight of crude oil, stirred for 30 min, and filtered. The filtrate was heated, added with 4% activated mixed adsorbent of kaolin and carbon (1:1) by weight of the crude oil, stirred for 30 min at 45° C., and then filtered. The filtrate was concentrated under a reduced pressure to recover the solvent, and washed again with purified water. After standing for 1 h, the lower waste water was removed. The upper oil was concentrated, in nitrogen atmosphere, by heating under vacuum and then underwent dry heat sterilization by vacuum at 165° C. for 1.5 h. After cooling, the oil was filtered through a 0.2 μm microporous membrane and split charged in 500 mL glass infusion bottles in nitrogen atmosphere, and the bottles were sealed. The *Coix* seed oil was thus obtained in a yield of 4.5%. Physicochemical constants were detected as: specific gravity at 20° C., 0.915; refractive index at 20° C., 1.471; acid value 0.18; iodine value 102; and saponification value 190.

Example 2 Preparation of *Coix* Seed Oil

Supercritical carbon dioxide extraction: *Coix* seeds were crushed into 60 mesh powder and extracted using 600 L×2 supercritical $CO_2$ extractors. *Coix* seed powder was put in an extractor. The $CO_2$ preheater, extractor and separation column were heated by jacketed circulating hot water, so that the extraction temperature and separation temperature reached 40° C. and 40° C., respectively, and the outlet temperatures of separator I and separator II were kept 20° C. and 15° C., respectively. Liquid $CO_2$ was pressed into the $CO_2$ preheater via a high pressure pump at a flow rate of 1 t/h, turning into a fluid in supercritical state. In the extractor, an oil was extracted into the $CO_2$ fluid at a pressure of 22 Mpa. Then the $CO_2$ fluid with this oil entered a separation column, and the pressure of the separation column was controlled to 8 Mpa to separate the oil. The $CO_2$ gas out from the separation column entered sequentially into separator I and separator II, in which the pressure was sustained at 6 Mpa and 5 Mpa, respectively. Impurities like water separated therefrom were discarded. The $CO_2$ gas returned to liquid $CO_2$ for reuse through a condenser. A continuous extraction for 2 h afforded a crude *Coix* seed oil.

Refining: To the crude *Coix* seed oil obtained by supercritical $CO_2$ extraction was added 65% petroleum ether (90° C.) based on the oil weight. 56% NaOH aqueous solution (2%) based on the oil weight was added according to the acid value. After stirring for 10 min, then standing for 22 h, the lower niger layer was removed. The upper layer was washed with purified water and let stand for 20 h. After the removal of the lower waste water, the upper layer went on a second washing. After standing for another 48 h, the lower waste water was removed, and the upper layer was demulsified by adding 90% acetone based on the oil weight. After standing for 2 h, the lower waste acetone was removed. The upper oil layer was added 8% of activated neutral alumina by weight of crude oil, stirred for 30 min, and filtered. The filtrate was heated, added with 6% of activated mixed adsorbent by weight of the crude oil, stirred for 30 min at 42° C., and then filtered. The filtrate was concentrated under a reduced pressure to recover the solvent, and washed again with purified water. After standing for 2 h, the lower waste water was removed. The upper oil was concentrated, in nitrogen atmosphere, by heating under vacuum and then underwent dry heat sterilization by vacuum at 170° C. for 1.5 h. After cooling, the oil was filtered through a 0.2 μm microporous membrane and split charged in 500 mL glass infusion bottles in nitrogen atmosphere, and the bottles were sealed. The *Coix* seed oil was thus obtained in a yield of 4.9%. Physicochemical constants were detected as: specific gravity at 20° C., 0.920; refractive index at 20° C., 1.473; acid value 0.19; iodine value 104; and saponification value 186.

Example 3 Preparation of *Coix* Seed Oil

Supercritical carbon dioxide extraction: *Coix* seeds were crushed into 100 mesh powder and extracted using 600 L×2 supercritical $CO_2$ extractors. *Coix* seed powder was put in an extractor. The $CO_2$ preheater, extractor and separation column were heated by jacketed circulating hot water, so that the extraction temperature and separation temperature reached 33° C. and 39° C., respectively, and the outlet temperatures of separator I and separator II were kept 30° C. and 20° C., respectively. Liquid $CO_2$ was pressed into the $CO_2$ preheater via a high pressure pump at a flow rate of 3 t/h, turning into a fluid in supercritical state. In the extractor, an oil was extracted into the $CO_2$ fluid at a pressure of 19 Mpa. Then the $CO_2$ fluid with this oil entered a separation column, and the pressure of the separation column was controlled to 9 Mpa to separate the oil. The $CO_2$ gas out from the separation column entered sequentially into separator I and separator II, in which the pressure was sustained at 5 Mpa and 4 Mpa, respectively. Impurities like water separated therefrom were discarded. The $CO_2$ gas returned to liquid $CO_2$ for reuse through a condenser. A continuous extraction for 3 h afforded a crude *Coix* seed oil.

Refining: To the crude *Coix* seed oil obtained by supercritical $CO_2$ extraction was added 65% petroleum ether (80° C.) based on the oil weight. 36% NaOH (2%) aqueous solution based on the oil weight was added according to the acid value. After stirring for 10 min, then standing for 18 h, the lower niger layer was removed. The upper layer was washed with purified water and let stand for 18 h. After the removal of the lower waste water, the upper layer went on a second washing. After standing for another 42 h, the lower waste water was removed, and the upper layer was demulsified by adding 75% acetone based on the oil weight. After standing for 2 h, the lower waste acetone was removed. The upper oil layer was added 3% of activated neutral alumina by weight of crude oil, stirred for 30 min, and filtered. The filtrate was heated, added with 2% of activated mixed adsorbent (ibid) by weight of the crude oil, stirred for 30 min at 47° C., and then filtered. The filtrate was concentrated under a reduced pressure to recover the solvent, and washed again with purified water. After standing for 1 h, the lower waste water was removed. The upper oil layer was concentrated, in nitrogen atmosphere, by heating under vacuum and then underwent dry heat sterilization by vacuum at 160° C. for 2 h. After cooling, the oil was filtered through a 0.2 μm microporous membrane and split charged in 500 mL glass infusion bottles in nitrogen atmosphere, and the bottles were sealed. The *Coix* seed oil was thus obtained in a yield of 4.7%. Physicochemical constants were detected as: specific gravity at 20° C., 0.918; refractive index at 20° C., 1.474; acid value 0.15; iodine value 100; and saponification value 194.

Example 4 Preparation of *Coix* Seed Oil

Supercritical carbon dioxide extraction: *Coix* seeds were crushed into 30 mesh powder and extracted using 600 L×2 supercritical $CO_2$ extractors. *Coix* seed powder was put in an extractor. The $CO_2$ preheater, extractor and separation column were heated by jacketed circulating hot water, so that the extraction temperature and separation temperature reached 35° C. and 42° C., respectively, and the outlet temperatures of separator I and separator II were kept at 40° C. and 30° C., respectively. Liquid $CO_2$ was pressed into the $CO_2$ preheater via a high pressure pump at a flow rate of 1.5 t/h, turning into a fluid in supercritical state. In the extractor, an oil was extracted into the $CO_2$ fluid at a pressure of 21 Mpa. Then the $CO_2$ fluid with this oil entered a separation column, and the pressure of the separation column was controlled to 10 Mpa to separate the oil. The $CO_2$ gas out from the separation column entered sequentially into separator I and separator II, in which the pressure was sustained at 7 Mpa and 5 Mpa, respectively. Impurities like water separated therefrom were discarded. The $CO_2$ gas returned to liquid $CO_2$ for reuse through a condenser. A continuous extraction for 2 h afforded a crude Coix seed oil.

Refining: To the crude Coix seed oil obtained by supercritical $CO_2$ extraction was added 65% petroleum ether (70° C.) based on the oil weight. 50% NaOH (2%) aqueous solution based on the oil weight was added according to the acid value. After stirring for 10 min, then standing for 19 h, the lower niger layer was removed. The upper layer was washed with purified water and let stand for 21 h. After the removal of the lower waste water, the upper layer went on a second washing. After standing for another 50 h, the lower waste water was removed, and the upper layer was demulsified by adding 85% acetone based on the oil weight. After standing for 4 h, the lower waste acetone was removed. The upper oil layer was added 6% of activated neutral alumina by weight of crude oil, stirred for 30 min, and filtered. The filtrate was heated, added with 5% activated mixed adsorbent (ibid) by weight of the crude oil, stirred for 30 min at 50° C., and then filtered. The filtrate was concentrated under a reduced pressure to recover the solvent, and washed again with purified water. After standing for 1 h, the lower waste water was removed. The upper oil layer was concentrated, in nitrogen atmosphere, by heating under vacuum and then underwent dry heat sterilization by vacuum at 162° C. for 2 h. After cooling, the oil was filtered through a 0.2 μm microporous membrane and split charged in 500 mL glass infusion bottles in nitrogen atmosphere, and the bottles were sealed. The Coix seed oil was thus obtained in a yield of 4.0%. Physicochemical constants were detected as: specific gravity at 20° C., 0.920; refractive index at 20° C., 1.471; acid value 0.16; iodine value 105; and saponification value 192.

Example 5 Preparation of Coix Seed Oil

Supercritical carbon dioxide extraction: Coix seeds were crushed into 40 mesh powder and extracted using 600 L×2 supercritical $CO_2$ extractors. Coix seed powder was put in an extractor. The $CO_2$ preheater, extractor and separation column were heated by jacketed circulating hot water, so that the extraction temperature and separation temperature reached 42° C. and 45° C., respectively, and the outlet temperatures of separator I and separator II were kept 35° C. and 25° C., respectively. Liquid $CO_2$ was pressed into the $CO_2$ preheater via a high pressure pump at a flow rate of 2.5 t/h, turning into a fluid in supercritical state. In the extractor, an oil was extracted into the $CO_2$ fluid at a pressure of 23 Mpa. Then the $CO_2$ fluid with this oil entered a separation column, and the pressure of the separation column was controlled to 8 Mpa to separate the oil. The $CO_2$ gas out from the separation column entered sequentially into separator I and separator II, in which the pressure was sustained at 6 Mpa and 4 Mpa, respectively. Impurities like water separated therefrom were discarded. The $CO_2$ gas returned to liquid $CO_2$ for reuse through a condenser. A continuous extraction for 2.5 h afforded a crude Coix seed oil.

Refining: To the crude Coix seed oil obtained by supercritical $CO_2$ extraction was added 65% petroleum ether (80° C.) based on the oil weight. 40% NaOH (2%) aqueous solution based on the oil weight was added according to the acid value. After stirring for 10 min, then standing for 24 h, the lower niger layer was removed. The upper layer was washed with purified water and let stand for 24 h. After the removal of the lower waste water, the upper layer went on a second washing. After standing for another 44 h, the lower waste water was removed, and the upper layer was demulsified by adding 70% acetone based on the oil weight. After standing for 3 h, the lower waste acetone was removed. The upper oil layer was added 4% activated neutral alumina by weight of crude oil, stirred for 30 min, and filtered. The filtrate was heated, added with 3% activated mixed adsorbent (ibid) by weight of the crude oil, stirred for 30 min at 40° C., and then filtered. The filtrate was concentrated under a reduced pressure to recover the solvent, and washed again with purified water. After standing for 1.5 h, the lower waste water was removed. The upper oil layer was concentrated, in nitrogen atmosphere, by heating under vacuum and then underwent dry heat sterilization by vacuum at 165° C. for 1.5 h. After cooling, the oil was filtered through a 0.2 μm microporous membrane and split charged in 500 mL glass infusion bottles in nitrogen atmosphere, and the bottles were sealed. The Coix seed oil was thus obtained in a yield of 4.3%. Physicochemical constants were detected as: specific gravity at 20° C., 0.916; refractive index at 20° C., 1.473; acid value 0.14; iodine value 101; and saponification value 192.

Example 6

8000 mg of Coix seed oil was dissolved in 10 ml n-hexane by using ultrasonic dissolving method, and prepared to be a Coix seed oil solution in acetone (50 mg/mL). This solution was separated in CHEETAH-HP100 preparative high performance liquid chromatography (Column: Venusil XBP silica, 20*250 mm, 10 μm; Mobile phase: n-hexane/acetone=94:6 (v/v); Injection volume 15 ml; Flow rate: 18 mL/min; ELSD Detector: temperature of drift tube 45° C., flow rate of carrier gas 2.0 L/min). Peak fraction at retention time of 15.8 min was collected and concentrated under vacuum at 30° C. The concentrated fraction was transferred into a 10 ml sample vial and blow-dried with nitrogen at ambient temperature to obtain a colourless oil, 1,3-diolein.

Q-TOF/MS: quasi-molecular ion peaks $[M+Na]^+$=m/z 643.5277 (Calcd.=643.5272, $C_{39}H_{72}O_5Na$), $\Omega$=4.

$^1$H-NMR data and $^{13}$C-NMR data are shown in Table 3.

TABLE 3

| $^1$H NMR and $^{13}$C NMR data (CDCl$_3$) | | |
|---|---|---|
| Position | $^1$H NMR | $^{13}$C NMR |
| C-1', 1" | | 174.0 |
| C-2', 2" | 2.33 (4H, t, J = 5.0 Hz) | 34.3 |
| C-3', 3" | | 25.0 |
| C-4', 4" | | 29.3 |
| C-5', 5" | | 29.3 |
| C-6', 6" | | 29.3 |
| C-7', 7" | | 29.8 |
| C-8', 8" | | 27.3 |
| C-9', 9" | 5.34 (2H, m) | 129.9 |
| C-10', 10" | 5.34 (2H, m) | 130.2 |
| C-11', 11" | | 27.3 |

TABLE 3-continued

¹H NMR and ¹³C NMR data (CDCl₃)

| Position | ¹H NMR | ¹³C NMR |
|---|---|---|
| C-12', 12" | | 29.9 |
| C-13', 13" | | 29.5 |
| C-14', 14" | | 29.7 |
| C-15', 15" | | 29.5 |
| C-16', 16" | | 32.1 |
| C-17', 17" | | 22.8 |
| C-18', 18" | 0.87 (6H, t, J = 5 Hz) | 14.3 |
| C-1 | 4.19 (2H, dd, J = 11.6, 4.8 Hz) | 65.2 |
|  | 4.13 (2H, dd, J = 11.6, 5.7 Hz) | |
| C-2 | 4.08 (1H, m) | 68.6 |
| C-3 | 4.19 (2H, dd, J = 11.6, 4.8 Hz) | 65.2 |
|  | 4.13 (2H, dd, J = 11.6, 5.7 Hz) | |

Example 7

8000 mg of *Coix* seed oil was dissolved in 10 ml n-hexane by using ultrasonic dissolving method, and prepared to be a *Coix* seed oil solution in acetone (50 mg/mL). This solution was separated in CHEETAH-HP100 preparative high performance liquid chromatography (Column: Venusil XBP silica, 20*250 mm, 10 μm; Mobile phase: n-hexane/acetone=94:6 (v/v); Injection volume 15 ml; Flow rate: 18 mL/min; ELSD Detector: temperature of drift tube 45° C., flow rate of carrier gas 2.0 L/min). Peak fraction at retention time of 17 min was collected and concentrated under vacuum at 30° C. The concentrated fraction was transferred into a 10 ml sample vial and blow-dried with nitrogen at ambient temperature to obtain a colourless oil, 1-linolein-3-olein.

Q-TOF/MS: quasi-molecular ion peaks [M+Na]⁺=m/z 641.5121 (Calcd.=641.5115, $C_{39}H_{70}O_5Na$), Ω=5.

¹H-NMR data and ¹³C-NMR data are shown in Table 4.

TABLE 4

¹H NMR and ¹³C NMR data (CDCl₃)

| Position | ¹H NMR | ¹³C NMR | Position | ¹H NMR | ¹³C NMR |
|---|---|---|---|---|---|
| C-1' | | 174.8 | C-1" | | 174.8 |
| C-2' | 2.35 (4H, t, J = 7.6 Hz) | 35.1 | C-2" | 2.35 (4H, t, J = 7.6 Hz) | 35.1 |
| C-3' | | 25.9 | C-3" | | 25.9 |
| C-4' | | 30.1 | C-4" | | 30.1 |
| C-5' | | 30.1 | C-5" | | 30.1 |
| C-6' | | 30.1 | C-6" | | 30.1 |
| C-7' | | 30.7 | C-7" | | 30.7 |
| C-8' | | 28.2 | C-8" | | 28.2 |
| C-9' | 5.39 (1H, m) | 131.0 | C-9" | 5.39 (1H, m) | 130.7 |
| C-10' | 5.39 (1H, m) | 129.1 | C-10" | 5.39 (1H, m) | 131.0 |
| C-11' | 2.80 (2H, t, J = 6.6 Hz) | 26.6 | C-11" | | 28.2 |
| C-12' | 5.39 (1H, m) | 128.9 | C-12" | | 30.8 |
| C-13' | 5.39 (1H, m) | 131.2 | C-13" | | 30.3 |
| C-14' | | 28.2 | C-14" | | 30.6 |
| C-15' | | 30.5 | C-15" | | 30.3 |
| C-16' | | 32.5 | C-16" | | 32.9 |
| C-17' | | 23.6 | C-17" | | 23.7 |
| C-18' | 0.91 (3H, t, J = 5.0 Hz) | 15.0 | C-18" | 0.92 (3H, t, J = 5.0 Hz) | 15.1 |
| C-1 | 4.21 (2H, dd, J = 11.5, 4.3 Hz) | 66.0 | | | |
|  | 4.16 (2H, dd, J = 11.5, 5.7 Hz) | | | | |
| C-2 | 4.11 (1H, m) | 69.4 | | | |
| C-3 | 4.21 (2H, dd, J = 11.5, 4.3 Hz) | 66.0 | | | |
|  | 4.16 (2H, dd, J = 11.5, 5.7 Hz) | | | | |

Example 8

8000 mg of *Coix* seed oil was dissolved in 10 ml n-hexane by using ultrasonic dissolving method, and prepared to be a *Coix* seed oil solution in acetone (50 mg/mL). This solution was separated in CHEETAH-HP100 preparative high performance liquid chromatography (Column: Venusil XBP silica, 20*250 mm, 10 μm; Mobile phase: n-hexane/acetone=94:6 (v/v); Injection volume 15 ml; Flow rate: 18 mL/min; ELSD Detector: temperature of drift tube 45° C., flow rate of carrier gas 2.0 L/min). Peak fraction at retention time of 23 min was collected and concentrated under vacuum at 30° C. The concentrated fraction was transferred into a 10 ml sample vial and blow-dried with nitrogen at ambient temperature to obtain a colourless oil, 1,2-diolein.

Q-TOF/MS: quasi-molecular ion peaks [M+Na]⁺=m/z 643.5277 (Calcd.=643.5272, $C_{39}H_{72}O_5Na$), Ω=4.

¹H-NMR data and ¹³C-NMR data are shown in Table 5.

TABLE 5

¹H NMR and ¹³C NMR data (CDCl₃)

| Position | ¹H NMR | ¹³C NMR |
|---|---|---|
| C-1' | | 173.9 |
| C-1" | | 173.5 |
| C-2' | 2.33 (4H, t, J = 5.0 Hz) | 34.2 |
| C-2" | | 34.4 |
| C-3' | | 25.0 |
| C-3" | | 25.1 |
| C-4', 4" | | 29.3 |
| C-5', 5" | | 29.3 |
| C-6', 6" | | 29.3 |
| C-7', 7" | | 29.8 |
| C-8', 8" | | 27.3 |
| C-9', 9" | 5.35 (2H, m) | 129.8 |
| C-10', 10" | 5.35 (2H, m) | 130.2 |
| C-11', 11" | | 27.3 |
| C-12', 12" | | 29.9 |
| C-13', 13" | | 29.5 |
| C-14', 14" | | 29.7 |
| C-15', 15" | | 29.5 |
| C-16', 16" | | 32.1 |
| C-17', 17" | | 22.7 |
| C-18', 18" | 0.88 (6H, t, J = 5 Hz) | 14.3 |
| C-1 | 4.32 (2H, dd, J = 12.0, 4.6 Hz) | 62.1 |
|  | 4.24 (2H, dd, J = 12.0, 5.6 Hz) | |
| C-2 | 5.08 (1H, m) | 72.3 |
| C-3 | 3.73 (2H, d, J = 3.2 Hz) | 61.8 |

Example 9

8000 mg of *Coix* seed oil was dissolved in 10 ml n-hexane by using ultrasonic dissolving method, and prepared to be a *Coix* seed oil solution in acetone (50 mg/mL). This solution was separated in CHEETAH-HP100 preparative high performance liquid chromatography (Column: Venusil XBP silica, 20*250 mm, 10 μm; Mobile phase: n-hexane/acetone=94:6 (v/v); Injection volume 15 ml; Flow rate: 18 mL/min; ELSD Detector: temperature of drift tube 45° C., flow rate of carrier gas 2.0 L/min). Peak fraction at retention time of 24.5 min was collected and concentrated under vacuum at 30° C. The concentrated fraction was transferred into a 10 ml sample vial and blow-dried with nitrogen at ambient temperature to obtain a colourless oil, 1-olein-2-linolein.

Q-TOF/MS: quasi-molecular ion peaks [M+Na]⁺=m/z 641.5121 (Calcd.=641.5115, $C_{39}H_{70}O_5Na$), Ω=5.

¹H-NMR data and ¹³C-NMR data are shown in Table 6.

TABLE 6

$^1$H NMR and $^{13}$C NMR data (CDCl$_3$)

| Position | $^1$H NMR | $^{13}$C NMR | Position | $^1$H NMR | $^{13}$C NMR |
|---|---|---|---|---|---|
| C-1' |  | 173.9 | C-1'' |  | 173.5 |
| C-2' | 2.33 (2H, t, J = 5.0 Hz) | 34.2 | C-2'' | 2.33 (2H, t, J = 5.0 Hz) | 34.4 |
| C-3' |  | 25.0 | C-3'' |  | 25.1 |
| C-4' |  | 29.3 | C-4'' |  | 29.3 |
| C-5' |  | 29.3 | C-5'' |  | 29.5 |
| C-6' |  | 29.3 | C-6'' |  | 29.3 |
| C-7' |  | 29.8 | C-7'' |  | 29.9 |
| C-8' |  | 27.3 | C-8'' |  | 27.4 |
| C-9' | 5.37 (1H, m) | 129.8 | C-9'' | 5.37 (1H, m) | 130.2 |
| C-10' | 5.37 (1H, m) | 130.2 | C-10'' | 5.37 (1H, m) | 128.2 |
| C-11' |  | 25.8 | C-11'' | 2.77 (2H, t, J = 6.5 Hz) | 25.8 |
| C-12' |  | 29.9 | C-12'' | 5.37 (1H, m) | 128.0 |
| C-13' |  | 29.5 | C-13'' | 5.37 (1H, m) | 130.4 |
| C-14' |  | 27.4 | C-14'' |  | 27.4 |
| C-15' |  | 29.5 | C-15'' |  | 29.8 |
| C-16' |  | 32.1 | C-16'' |  | 31.7 |
| C-17' |  | 22.8 | C-17'' |  | 22.7 |
| C-18' | 0.89 (3H, t, J = 6.8 Hz) | 14.3 | C-18'' | 0.88 (3H, t, J = 6.8 Hz) | 14.2 |
| C-1 | 4.32 (1H, dd, J = 11.9, 4.5 Hz) 4.23 (1H, dd, J = 11.9, 5.6 Hz) | 62.1 |  |  |  |
| C-2 | 5.08 (1H, m) | 72.3 |  |  |  |
| C-3 | 3.73 (2H, d, J = 3.2 Hz) | 61.8 |  |  |  |

TABLE 7

$^1$H NMR and $^{13}$C NMR data (CDCl$_3$)

| Position | $^1$H NMR | $^{13}$C NMR | Position | $^1$H NMR | $^{13}$C NMR |
|---|---|---|---|---|---|
| C-1' |  | 173.9 | C-1'' |  | 173.5 |
| C-2' | 2.32 (4H, t, J = 5.0 Hz) | 34.2 | C-2'' | 2.35 (2H, t, J = 5.0 Hz) | 34.4 |
| C-3' |  | 25.0 | C-3'' |  | 25.1 |
| C-4' |  | 29.3 | C-4'' |  | 29.3 |
| C-5' |  | 29.5 | C-5'' |  | 29.5 |
| C-6' |  | 29.3 | C-6'' |  | 29.3 |
| C-7' |  | 29.9 | C-7'' |  | 29.9 |
| C-8' |  | 27.4 | C-8'' |  | 27.4 |
| C-9' | 5.37 (1H, m) | 130.2 | C-9'' | 5.37 (1H, m) | 130.2 |
| C-10' | 5.37 (1H, m) | 128.2 | C-10'' | 5.37 (1H, m) | 128.2 |
| C-11' | 2.77 (4H, t, J = 6.5 Hz) | 25.8 | C-11'' | 2.77 (2H, t, J = 6.5 Hz) | 25.8 |
| C-12' | 5.37 (1H, m) | 128.0 | C-12'' | 5.37 (1H, m) | 128.0 |
| C-13' | 5.37 (1H, m) | 130.4 | C-13'' | 5.37 (1H, m) | 130.4 |
| C-14' |  | 27.4 | C-14'' |  | 27.4 |
| C-15' |  | 29.8 | C-15'' |  | 29.8 |
| C-16' |  | 31.7 | C-16'' |  | 31.7 |
| C-17' |  | 22.7 | C-17'' |  | 22.7 |
| C-18' | 0.89 (3H, t, J = 6.8 Hz) | 14.2 | C-18'' | 0.89 (3H, t, J = 6.8 Hz) | 14.2 |
| C-1 | 4.32 (1H, dd, J = 11.9, 4.6 Hz) 4.24 (1H, dd, J = 12.0, 5.6 Hz) | 62.1 |  |  |  |
| C-2 | 5.08 (1H, m) | 72.3 |  |  |  |
| C-3 | 3.73 (2H, d, J = 3.2 Hz) | 61.8 |  |  |  |

Example 10

8000 mg of *Coix* seed oil was dissolved in 10 ml n-hexane by using ultrasonic dissolving method, and prepared to be a *Coix* seed oil solution in acetone (50 mg/mL). This solution was separated in CHEETAH-HP100 preparative high performance liquid chromatography (Column: Venusil XBP silica, 20*250 mm, 10 µm; Mobile phase: n-hexane/acetone=94:6 (v/v); Injection volume 15 ml; Flow rate: 18 mL/min; ELSD Detector: temperature of drift tube 45° C., flow rate of carrier gas 2.0 L/min). Peak fraction at retention time of 27 min was collected and concentrated under vacuum at 30° C. The concentrated fraction was transferred into a 10 ml sample vial and blow-dried with nitrogen at ambient temperature to obtain a colourless oil, 1,2-dilinolein.

Q-TOF/MS: quasi-molecular ion peaks [M+Na]$^+$=m/z 639.4964 (Calcd.=639.4959, $C_{39}H_{68}O_5Na$), Ω=6.

$^1$H-NMR data and $^{13}$C-NMR data are shown in Table 7.

Example 11 Isolation and Identification of Trilinolein

Isolation was carried out on P3000A preparative high performance liquid chromatography (Column: Superstar Benetnach™ $C_{18}$, 20 mm×150 mm, 5 µm; Mobile phase A: acetonitrile, Mobile phase B: acetonitrile/tetrahydrofuran (1:1)). *Coix* seed oil solution (50 mg/mL) was prepared with mobile phase B, and the injection volume for each separation was 1.5 mL. Gradient conditions were: mobile phase B: 0-27 min: 50%-60%, 27-35 min: 90%, 35-45 min: 100%; and flow rate: 18 mL/min. UV detection was conducted at 208 nm. Peak fractions at retention time of 12.6-14.2 min were collected, and concentrated using a rotary evaporator under vacuum in nitrogen. Residues were transferred with chloroform to a 10 mL vial, and dried in a vacuum oven at 35° C. for 6 h. After filling with nitrogen, the dried samples were frozen in a refrigerator, to give the trilinolein.

HR-EI-MS: m/z=878.7344 (Calcd.=878.7363, $C_{57}H_{98}O_6$), Degree of unsaturation=9.

IR (KBr film): 1746, 1170, 1098; 2928, 2856, 724; 3008, 1655 cm$^{-1}$ (weak).

$^1$H-NMR data are shown in Table 8.

$^{13}$C-NMR data are shown in Table 9.

TABLE 8

$^1$H-NMR spectral data (CDCl$_3$) of the compounds of Examples 6-13

| No. | G-H | H | 2-H | 3-H | 4-H | 5-H | 6-H | 7-H | 8-H | 9-H | 10-H | 11-H | 12-H | 13-H | 14-H | 15-H | 16-H | 17-H | 18-H |
|---|---|---|---|---|---|---|---|---|---|---|---|---|---|---|---|---|---|---|---|
| A LLL | α β α' | 4.30 5.27 4.15 | 2.32 | 1.61 |  | 1.32 |  |  | 2.05 | 5.36 | 2.77 | 5.36 | 2.05 |  |  | 1.32 |  |  | 0.89 |
| B OLL | α β α' | 4.29 5.27 4.14 | 2.32 | 1.61 |  | 1.33 |  |  | 2.04 | 5.37 | 2.77 | 5.37 | 2.04 | 1.33 |  |  |  |  | 0.88 |
| C | α | 4.30 |  |  |  |  |  |  | 2.05 | 5.36 | 2.77 | 5.36 | 2.05 |  |  | 1.31 |  |  | 0.88 |

TABLE 8-continued

¹H-NMR spectral data (CDCl₃) of the compounds of Examples 6-13

| No. | G-H | H | 2-H | 3-H | 4-H | 5-H | 6-H | 7-H | 8-H | 9-H | 10-H | 11-H | 12-H | 13-H | 14-H | 15-H | 16-H | 17-H | 18-H |
|---|---|---|---|---|---|---|---|---|---|---|---|---|---|---|---|---|---|---|---|
| PLL | β | 5.27 | 2.31 | 1.61 | 1.31 | | | | | | | | | | | | | | |
| | α' | 4.15 | | | | | | | 1.31 | | | | | 1.31 | | | 0.88 | | |
| D | α | 4.30 | | | | | | | | | 2.05 | | | 1.32 | | | | | |
| OLO | β | 5.27 | 2.32 | 1.61 | 1.32 | | | | 2.05 | 5.36 | | 2.77 | 5.36 | 2.05 | | | 1.32 | | 0.89 |
| | α' | 4.15 | | | | | | | | | | | | | | | | | |
| E | α | 4.15 | | | | | | | 2.04 | 5.35 | 2.04 | | 1.28 | | | | 1.28 | | 0.88 |
| PLO | β | 5.27 | 2.31 | 1.61 | 1.28 | | | | | | | 2.77 | 5.35 | 2.04 | 1.28 | | | | |
| | α' | 4.30 | | | | | | | 1.28 | | | | | | | | 0.88 | | |
| F | α | 4.15 | | | | | | | 1.28 | | | | | | | | 0.88 | | |
| PLP | β | 5.27 | 2.31 | 1.61 | 1.28 | | | | 2.05 | 5.36 | 2.77 | 5.36 | 2.05 | | | 1.28 | | | 0.88 |
| | α' | 4.30 | | | | | | | | | 1.28 | | | | | | 0.88 | | |
| G | α | 4.15 | | | | | | | | | | | | | | | | | |
| OOO | β | 5.27 | 2.31 | 1.61 | 1.28 | | | | 2.00 | 5.34 | 2.00 | | | 1.28 | | | | | 0.88 |
| | α' | 4.30 | | | | | | | | | | | | | | | | | |
| H | α | 4.15 | | | | | | | 2.04 | 5.34 | 2.04 | | 1.27 | | | | | | 0.88 |
| POO | β | 5.27 | 2.31 | 1.61 | 1.28 | | | | | | | | | | | | | | |
| | α' | 4.30 | | | | | | | | 1.27 | | | | | | | 0.88 | | |

A: trilinolein, B: 1-olein-2,3-dilinolein, C: 1-palmitin-2,3-dilinolein, D: 1,3-diolein-2-linolein, E: 1-palmitin-2-linolein-3-olein, F: 1,3-dipalmitin-2-linolein, G: triolein, H: 1-palmitin-2,3-diolein.

TABLE 9

¹³C-NMR spectral data (CDCl₃) of the compounds of Examples 6-13

| No. | Abb. | C1—C | C-1 | C-2 | C-3 | C-4 | C-5 | C-6 | C-7 | C-8 | C-9 | C-10 |
|---|---|---|---|---|---|---|---|---|---|---|---|---|
| A | α | 62.12 | 173.28 | 34.05 | 24.86 | | 29.05~29.62 | | | 27.21 | 130.01 | 128.08 |
| LLL | β | 68.91 | 172.87 | 34.21 | 24.90 | | | | | | 129.98 | 128.09 |
| B | α | 62.12 | 173.28 | 34.04 | 24.86 | | 29.07~29.79 | | | 27.22 | 130.03 | 128.03 |
| OLL | β | 68.89 | 172.87 | 34.21 | 24.90 | | | | | 27.19 | 130.00 | 128.10 |
| | α' | | 173.29 | | | | | | | | 129.73 | 130.03 |
| C | α | 62.12 | 173.30 | 34.04 | 24.89 | | 29.06~29.72 | | | 27.21 | 130.02 | 128.08 |
| PLL | β | 68.90 | 172.88 | 34.20 | 24.85 | | | | | | 129.99 | 128.09 |
| | α' | | 173.34 | 34.07 | 24.38 | | | | | | 29.06~29.72 | |
| D | α | 62.12 | 173.29 | 34.05 | 24.86 | | 29.07~29.79 | | | 27.20 | 129.73 | 130.03 |
| OLO | β | 68.89 | 172.87 | 34.21 | 24.90 | | | | | 27.22 | 130.00 | 128.10 |
| E | α | 62.11 | 173.28 | 34.04 | 24.85 | | 29.06~29.78 | | | 27.18 | 129.71 | 130.01 |
| PLO | β | 63.91 | 172.86 | 34.20 | 24.87 | | | | | 27.21 | 129.98 | 128.09 |
| | α' | | 173.32 | 34.06 | 24.98 | | | | | | 29.06~29.78 | |
| F | α | 62.09 | 173.32 | 34.05 | 24.86 | | 29.05~29.70 | | | | 29.05~29.70 | |
| PLP | β | 63.89 | 172.86 | 34.19 | 24.88 | | | | | 27.20 | 129.97 | 128.08 |
| G | α | 62.12 | 173.29 | 34.04 | 24.86 | | 29.07~9.78 | | | 27.19 | 129.72 | 130.02 |
| OOO | β | 68.90 | 172.87 | 34.21 | 24.90 | | | | | | 129.69 | 130.03 |
| H | α | 62.12 | 173.31 | 34.04 | 24.88 | | 29.06~29.78 | | | 27.19 | 129.72 | 130.02 |
| POO | β | 68.90 | 172.90 | 34.21 | 24.86 | | | | | | 129.69 | 130.03 |
| | α' | | 173.35 | 34.06 | 24.90 | | | | | | 29.06~29.78 | |

| No. | Abb. | C-11 | C-12 | C-13 | C-14 | C-15 | C-16 | C-17 | C-18 |
|---|---|---|---|---|---|---|---|---|---|
| A | α | 25.64 | 127.91 | 130.22 | 27.21 | 29.05~29.62 | 31.53 | 22.58 | 14.07 |
| LLL | β | | 127.90 | | | | | | |
| B | α | 25.65 | 127.91 | 130.24 | 27.24 | 29.07~29.79 | 31.55 | 22.60 | 14.10 |
| OLL | β | | 127.90 | | | | | | |
| | α' | 27.22 | | | 29.07~29.79 | | 31.93 | 22.71 | 14.14 |
| C | α | 25.64 | 127.909 | 130.236 | | 29.06~29.72 | 31.54 | 22.59 | 14.09 |
| PLL | β | | 127.898 | 130.236 | | | | | |
| | α' | | | | 31.95 | | 22.71 | | 14.14 |
| D | α | 27.24 | | | 29.07~29.79 | | 31.93 | 22.71 | 14.14 |
| OLO | β | 25.65 | 127.90 | 130.24 | 27.24 | 29.07~29.79 | 31.55 | 22.60 | 14.10 |
| E | α | 27.21 | | | 29.06~29.78 | | 31.92 | 22.69 | 14.12 |
| PLO | β | 25.64 | 127.90 | 130.22 | 27.23 | 29.06~29.78 | 31.54 | 22.58 | 14.07 |
| | α' | | | | 31.94 | | 22.71 | | 14.12 |
| F | α | | 29.05~29.70 | | 31.93 | | 22.69 | | 14.12 |
| PLP | β | 25.63 | 127.89 | 130.22 | 27.20 | 29.05~29.70 | 31.53 | 22.58 | 14.07 |
| G | α | 27.24 | | | 29.07~29.78 | | 31.92 | 22.70 | 14.12 |
| OOO | β | | | | | | | | |
| H | α | 27.24 | | | 29.06~29.78 | | 31.92 | | |
| POO | β | | | | | | | 22.70 | 14.12 |
| | α' | | 29.06~29.78 | | 31.94 | 22.70 | 14.12 | | |

A: trilinolein, B: 1-olein-2,3-dilinolein, C: 1-palmitin-2,3-dilinolein, D: 1,3-diolein-2-linolein, E: 1-palmitin-2-linolein-3-olein, F: 1,3-dipalmitin-2-linolein, G: triolein, H: 1-palmitin-2,3-diolein.

Example 12 Isolation and Identification of 1-Olein-2,3-Dilinolein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). Coix seed oil solution (50 mg/mL) was prepared with mobile phase B, and the injection volume for each separation was 1.5 mL. Gradient conditions were: mobile phase B: 0-27 min: 50%-60%, 27-35 min: 90%, 35-45 min: 100%; and flow rate: 18 mL/min. UV detection was conducted at 208 nm. Peak fractions at retention time of 15.4-17.3 min were collected, and concentrated using a rotary evaporator under vacuum in nitrogen. Residues were transferred with chloroform to a 10 mL vial, and dried in a vacuum oven at 35° C. for 6 h. After filling with nitrogen, the dried samples were frozen in a refrigerator, to give 1-olein-2,3-dilinolein.

HR-EI-MS: m/z=880.7518 (Calcd.=854.7363, $C_{55}H_{98}O_6$), Degree of unsaturation=7.

IR (KBr film): 1747, 1164, 1098; 2925, 2854, 723; 3008, 1655 $cm^{-1}$ (weak).

$^1$H-NMR data are shown in Table 8.

$^{13}$C-NMR data are shown in Table 9.

Example 13 Isolation and Identification of 1-Palmitin-2,3-Dilinolein

Preliminary isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). A solution of Coix seed oil (50 mg/mL) was prepared with mobile phase B, and the injection volume for each separation was 1.5 mL. Gradient conditions were: mobile phase B: 0-27 min: 50%-60%, 27-35 min: 90%, 35-45 min: 100%; and flow rate: 18 mL/min. UV detection was conducted at 208 nm. Peak fractions at retention time of 17.4-18.1 min were collected, and concentrated using a rotary evaporator under vacuum in nitrogen, to give a crude product.

The second purification was proceeded on Superstar Benetnach™ $C_{18}$ Column (10 mm×250 mm, 5 μm) with mobile phase A: acetonitrile and mobile phase B: acetonitrile/tetrahydrofuran (1:1). A solution of the above crude product (20 mg/mL) was prepared with mobile phase B, and the injection volume for each separation was 1.5 mL. Gradient conditions were: mobile phase B: 0-23 min: 50%-60%, 32-43 min: 60%-90%, 43-60 min: 100%; and flow rate: 3 mL/min. UV detection was conducted at 208 nm. Peak fractions at retention time of 31.2-34.7 min were collected, and concentrated using a rotary evaporator under vacuum in nitrogen. Residues were transferred with chloroform to a 10 mL vial, and dried in a vacuum oven at 35° C. for 6 h. After filling with nitrogen, the dried samples were frozen in a refrigerator, to give 1-palmitin-2,3-dilinolein.

HR-EI-MS: m/z=854.7370 (Calcd.=854.7363, $C_{55}H_{98}O_6$), Degree of unsaturation=7.

IR (KBr Film): 1746, 1165, 1095; 2926, 2854, 722; 3009, 1648 $cm^{-1}$ (weak).

$^1$H-NMR data are shown in Table 8.

$^{13}$C-NMR data are shown in Table 9.

Example 14 Isolation and Identification of 1,3-Diolein-2-Linolein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). Coix seed oil solution (50 mg/mL) was prepared with mobile phase B, and the injection volume for each separation was 1.5 mL. Gradient conditions were: mobile phase B: 0-27 min: 50%-60%, 27-35 min: 90%, 35-45 min: 100%; and flow rate: 18 mL/min. UV detection was conducted at 208 nm. Peak fractions at retention time of 18.4-20.2 min were collected, and concentrated using a rotary evaporator under vacuum in nitrogen. Residues were transferred with chloroform to a 10 mL vial, and dried in a vacuum oven at 35° C. for 6 h. After filling with nitrogen, the dried samples were frozen in a refrigerator, to give 1-olein-2,3-dilinolein.

HR-EI-MS: m/z=882.7678 (Calcd.=882.7672, $C_{57}H_{102}O_6$), Degree of unsaturation=7.

IR (KBr film): 1747, 1163, 1097; 2925, 2855, 723; 3007, 1655 $cm^{-1}$ (weak).

$^1$H-NMR data are shown in Table 8.

$^{13}$C-NMR data are shown in Table 9.

Example 15 Isolation and Identification of 1-Palmitin-2-Linolein-3-Olein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). Coix seed oil solution (50 mg/mL) was prepared with mobile phase B, and the injection volume for each separation was 1.5 mL. Gradient conditions were: mobile phase B: 0-27 min: 50%-60%, 27-35 min: 90%, 35-45 min: 100%; and flow rate: 18 mL/min. UV detection was conducted at 208 nm. Peak fractions at retention time of 20.3-21.4 min were collected, and concentrated using a rotary evaporator under vacuum in nitrogen. Residues were transferred with chloroform to a 10 mL vial, and dried in a vacuum oven at 35° C. for 6 h. After filling with nitrogen, the dried samples were frozen in a refrigerator, to give 1-palmitin-2-linolein-3-olein.

HR-EI-MS: m/z=856.7519 (Calcd.=856.7513, $C_{55}H_{100}O_6$), Degree of unsaturation=6.

IR (KBr film): 1747, 1164, 1098; 2925, 2854, 723; 3008, 1655 $cm^{-1}$ (weak).

$^1$H-NMR data are shown in Table 8.

$^{13}$C-NMR data are shown in Table 9.

Example 16 Isolation and Identification of 1,3-Dipalmitin-2-Linolein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). Coix seed oil solution (50 mg/mL) was prepared with mobile phase B, and the injection volume for each separation was 1.5 mL. Gradient conditions were: mobile phase B: 0-27 min: 50%-60%, 27-35 min: 90%, 35-45 min: 100%; and flow rate: 18 mL/min. UV detection was conducted at 208 nm. Peak fractions at retention time of 25.7-26.2 min were collected, and concentrated using a rotary evaporator under vacuum in nitrogen. Residues were transferred with chloroform to a 10 mL vial, and dried in a vacuum oven at 35° C. for 6 h. After filling with nitrogen, the dried samples were frozen in a refrigerator, to give 1,3-dipalmitin-2-linolein.

HR-EI-MS: m/z=830.7371 (Calcd.=830.7363, $C_{53}H_{98}O_6$), Degree of unsaturation=5.

IR (KBr film): 1747, 1164, 1098; 2925, 2854, 723; 3008, 1655 cm$^{-1}$ (weak).

$^1$H-NMR data are shown in Table 8.

$^{13}$C-NMR data are shown in Table 9.

Example 17 Isolation and Identification of Triolein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). *Coix* seed oil solution (50 mg/mL) was prepared with mobile phase B, and the injection volume for each separation was 1.5 mL. Gradient conditions were: mobile phase B: 0-27 min: 50%-60%, 27-35 min: 90%, 35-45 min: 100%; and flow rate: 18 mL/min. UV detection was conducted at 208 nm. Peak fractions at retention time of 26.6-27.7 min were collected, and concentrated using a rotary evaporator under vacuum in nitrogen. Residues were transferred with chloroform to a 10 mL vial, and dried in a vacuum oven at 35° C. for 6 h. After filling with nitrogen, the dried samples were frozen in a refrigerator, to give triolein.

HR-EI-MS: m/z=884.7851 (Calcd.=884.7833, $C_{57}H_{104}O_6$), Degree of unsaturation=6.

IR (KBr film): 1749, 1165, 1095; 2925, 2854, 723; 3004, 1654 cm$^{-1}$ (weak).

$^1$H-NMR data are shown in Table 8.

$^{13}$C-NMR data are shown in Table 9.

Example 18 Isolation and Identification of 1-Palmitin-2,3-Diolein

Preliminary isolation was carried out on P3000A preparative high performance liquid chromatography (Column: Superstar Benetnach™ C18, 20 mm×150 mm, 5 μm; Mobile phase A: acetonitrile; Mobile phase B: acetonitrile/tetrahydrofuran (1:1)). A solution of *Coix* seed oil (50 mg/mL) was prepared with mobile phase B, and the injection volume for each separation was 1.5 mL. Gradient conditions were: mobile phase B: 0-27 min: 50%-60%, 27-35 min: 90%, 35-45 min: 100%; and flow rate: 18 mL/min. UV detection was conducted at 208 nm. Peak fractions at retention time of 28.2-29.3 min were collected, and concentrated using a rotary evaporator under vacuum in nitrogen, to give crude product.

The second purification was proceeded on Superstar Benetnach™ $C_{18}$ Column (10 mm×250 mm, 5 μm) with mobile phase A: acetonitrile and mobile phase B: acetonitrile/tetrahydrofuran (1:1). A solution of the above crude product (20 mg/mL) was prepared with mobile phase B, and the injection volume for each separation was 1.5 mL. Gradient conditions were: mobile phase B: 0-23 min: 50%-60%, 32-43 min: 60%-90%, 43-60 min: 100%; and flow rate: 3 mL/min. UV detection was conducted at 208 nm. Peak fractions at retention time of 32.9-35.1 min were collected, and concentrated using a rotary evaporator under vacuum in nitrogen. Residues were transferred with chloroform to a 10 mL vial, and dried in a vacuum oven at 35° C. for 6 h. After filling with nitrogen, the dried samples were frozen in a refrigerator, to give 1-palmitin-2,3-diolein.

HR-EI-MS: m/z=858.7672 (Calcd.=858.7676, $C_{55}H_{102}O_6$), Degree of unsaturation=5.

IR (KBr film): 1747, 1166, 1095; 2926, 2854, 722; 3003, 1654 cm$^{-1}$ (weak).

$^1$H-NMR data are shown in Table 8.

$^{13}$C-NMR data are shown in Table 9.

Example 19 Preparation of 1,3-dipalmitin-2-olein

*Coix* seed oil solution prepared in tetrahydrofuran (750 mg/mL) was preliminarily separated in CHEETAH-HP100 preparative high performance liquid chromatography (Column: Venusil XBP C18 (2), 50*250 mm, 5 μm, 100 Å; Mobile phase: acetonitrile/tetrahydrofuran=78:22 (v/v); Injection volume 2 ml; Flow rate: 80 mL/min; UV detection wavelength: 205 nm/280 nm). Peak fractions at retention time of 29-38 min were collected, and concentrated under vacuum in nitrogen atmosphere in a rotary evaporator to give a crude product.

The second purification was proceeded on Venusil XBP C18(L) Column (30*150 mm, 5 μm 150 Å) with acetonitrile: dichloromethane (65/35) as the mobile phase in a flow rate of 32 mL/min. A solution of the above crude product (10 mg/mL) was prepared in dichloromethane, and the injection volume for each separation was 2 mL. UV detection was conducted at 205 nm/280 nm. Peak fraction at retention time of 15 min was collected, and concentrated under vacuum in nitrogen atmosphere in a rotary evaporator. Residues were transferred with chloroform to a 10 mL vial, and dried in a vacuum oven at 35° C. for 6 h. After filling with nitrogen, the dried sample, 1,3-dipalmitin-2-olein, was frozen in a refrigerator.

HR-EI-MS: m/z=832.7542 (Calcd.=832.7566, $C_{53}H_{100}O_6$), Degree of unsaturation=4.

IR (KBr film): 1747, 1166, 1095; 2925, 2854, 722; 3003, 1654 cm$^{-1}$ (week).

$^1$H-NMR (CDCl$_3$) data are shown in Table 10.

TABLE 10

$^1$H-NMR spectral data of the compound of Example 19

| Position | Chemical shift | Amount of H, Spike & coupling constant |
|---|---|---|
| H—C=C | 5.34 | 2H, m |
| CH—OCO | 5.26 | 1H, m |
| —CH$_2$—OCO | 4.29 | 2H, dd, 12.0, 4.4 |
| —CH$_2$—OCO | 4.14 | 2H, d, 12.0, 6.0 |
| —CH2COO | 2.31 | 2H, t, 7.6 |
| —CH2COO | 2.31 | 4H, t, 7.6 |
| —CH$_2$—CH= | 2.00 | 4H, m |
| —CH$_2$CH$_2$COO | 1.60 | 6H, m |
| —CH$_2$ | 1.27 | 68H, m |
| —CH$_3$ | 0.87 | 9H, t, 6.8 |

$^{13}$C-NMR (CDCl$_3$) data are shown in Table 11.

TABLE 11

$^{13}$C-NMR (CDCl$_3$) spectral data of the compound of Example 19

| Position | | Chemical shift |
|---|---|---|
| C1 | 1 | 173.282 |
| | 2 | 172.839 |
| | 3 | 173.282 |
| C2 | 1 | 34.026 |
| | 2 | 34.179 |
| | 3 | 34.026 |
| C3 | 1 | 24.848 |
| | 2 | 24.848 |
| | 3 | 24.848 |
| C4 | 1 | 29.750~29.040 |
| | 2 | 29.750~29.040 |
| | 3 | 29.750~29.040 |

TABLE 11-continued

¹³C-NMR (CDCl₃) spectral data of the compound of Example 19

| Position | | Chemical shift |
|---|---|---|
| C5 | 1 | 29.750~29.040 |
| | 2 | 29.750~29.040 |
| | 3 | 29.750~29.040 |
| C6 | 1 | 29.750~29.040 |
| | 2 | 29.750~29.040 |
| | 3 | 29.750~29.040 |
| C7 | 1 | 29.750~29.040 |
| | 2 | 29.750~29.040 |
| | 3 | 29.750~29.040 |
| C8 | 1 | 29.750~29.040 |
| | 2 | 27.159 |
| | 3 | 29.750~29.040 |
| C9 | 1 | 29.750~29.040 |
| | 2 | 129.687 |
| | 3 | 29.750~29.040 |
| C10 | 1 | 29.750~29.040 |
| | 2 | 129.999 |
| | 3 | 29.750~29.040 |
| C11 | 1 | 29.750~29.040 |
| | 2 | 27.205 |
| | 3 | 29.750~29.040 |
| C12 | 1 | 29.750~29.040 |
| | 2 | 29.750~29.040 |
| | 3 | 29.750~29.040 |
| C13 | 1 | 29.750~29.040 |
| | 2 | 29.750~29.040 |
| | 3 | 29.750~29.040 |
| C14 | 1 | 31.895 |
| | 2 | 29.750~29.040 |
| | 3 | 31.895 |
| C15 | 1 | 22.672 |
| | 2 | 29.750~29.040 |
| | 3 | 22.672 |
| C16 | 1 | 14.099 |
| | 2 | 31.895 |
| | 3 | 14.099 |
| C17 | 2 | 22.672 |
| C18 | 2 | 14.099 |
| CHO | | 68.852 |
| CH2O | | 62.076 |

Example 20 Preparation of 1,2-Diolein-3-Stearin

*Coix* seed oil solution prepared in tetrahydrofuran (750 mg/mL) was preliminarily separated in CHEETAH-HP100 preparative high performance liquid chromatography (Column: Venusil XBP C18 (2), 50*250 mm, 5 μm, 100 Å; Mobile phase: acetonitrile/tetrahydrofuran=78:22 (v/v); Injection volume 2 ml (1.5 g); Flow rate: 80 mL/min; UV detection wavelength: 205 nm/280 nm). Peak fractions at retention time of 29-38 min were collected, and concentrated under vacuum in nitrogen atmosphere in a rotary evaporator, to give a crude product.

The second purification was proceeded on Venusil XBP C18(L) Column (30*150 mm, 5 μm 150 Å) with acetonitrile:dichloromethane (65/35) as the mobile phase in a flow rate of 32 mL/min. A solution of the above crude product (10 mg/mL) was prepared in dichloromethane, and the injection volume for each separation was 2 mL. UV detection was conducted at 205 nm/280 nm. Peak fraction at retention time of 17 min was collected, and concentrated under vacuum in nitrogen atmosphere in a rotary evaporator. Residues were transferred with chloroform to a 10 mL vial, and dried in a vacuum oven at 35° C. for 6 h. After filling with nitrogen, the dried sample, 1,2-diolein-3-stearin, was frozen in a refrigerator.

HR-EI-MS: m/z=886.8011 (Calcd.=886.7991, $C_{57}H_{106}O_6$), Degree of unsaturation=5.

IR (KBr film): 1747, 1166, 1095; 2926, 2856, 722; 3003, 1654 cm$^{-1}$ (week).

¹H-NMR (CDCl₃) data are shown in Table 12.

TABLE 12

¹H-NMR spectral data of the compound of Example 20

| Position | Chemical shift | Amount of H, Spike & coupling constant |
|---|---|---|
| H—C=C | 5.35 | 4H, m |
| β-CH—OCO | 5.26 | 1H, m |
| α-CH₂—OCO | 4.29 | 2H, dd, 11.6, 4.0 |
| α-CH₂—OCO | 4.14 | 2H, d, 12.0, 6.0 |
| —CH2COO | 2.31 | 2H, t, 7.6 |
| —CH2COO | 2.31 | 4H, t, 7.6 |
| —CH₂—CH= | 2.01 | 8H, m |
| —CH₂CH₂COO | 1.60 | 6H, m |
| —CH₂ | 1.27 | 74H, m |
| —CH₃ | 0.87 | 9H, t, 6.8 |

¹³C-NMR (CDCl₃) data are shown in Table 13.

TABLE 13

¹³C-NMR (CDCl₃) spectral data of the compound of Example 20

| Position | | Chemical shift |
|---|---|---|
| C1 | 1 | 173.258 |
| | 2 | 172.839 |
| | 3 | 173.282 |
| C2 | 1 | 34.028 |
| | 2 | 34.179 |
| | 3 | 34.028 |
| C3 | 1 | 24.848 |
| | 2 | 24.848 |
| | 3 | 24.848 |
| C4 | 1 | 30.00~29.00 |
| | 2 | 30.00~29.00 |
| | 3 | 30.00~29.00 |
| C5 | 1 | 30.00~29.00 |
| | 2 | 30.00~29.00 |
| | 3 | 30.00~29.00 |
| C6 | 1 | 30.00~29.00 |
| | 2 | 30.00~29.00 |
| | 3 | 30.00~29.00 |
| C7 | 1 | 30.00~29.00 |
| | 2 | 30.00~29.00 |
| | 3 | 30.00~29.00 |
| C8 | 1 | 27.159 |
| | 2 | 27.159 |
| | 3 | 29.00~30.00 |
| C9 | 1 | 129.687 |
| | 2 | 129.669 |
| | 3 | 29.00~30.00 |
| C10 | 1 | 129.999 |
| | 2 | 129.999 |
| | 3 | 29.00~30.00 |
| C11 | 1 | 27.206 |
| | 2 | 27.206 |
| | 3 | 29.00~30.00 |
| C12 | 1 | 29.00~30.00 |
| | 2 | 29.00~30.00 |
| | 3 | 29.00~30.00 |
| C13 | 1 | 29.00~30.00 |
| | 2 | 29.00~30.00 |
| | 3 | 29.00~30.00 |
| C14 | 1 | 29.00~30.00 |
| | 2 | 29.00~30.00 |
| | 3 | 31.895 |
| C15 | 1 | 29.00~30.00 |
| | 2 | 29.00~30.00 |
| | 3 | 22.672 |
| C16 | 1 | 31.895 |
| | 2 | 31.895 |
| | 3 | 31.895 |

TABLE 13-continued $^{13}$C-NMR (CDCl$_3$) spectral data of the compound of Example 20

| Position | | Chemical shift |
|---|---|---|
| C17 | 1 | 22.672 |
| | 2 | 22.672 |
| | 3 | 22.672 |
| C18 | 1 | 14.099 |
| | 2 | 14.099 |
| | 3 | 14.099 |
| β-CHO— | | 68.852 |
| α-CH2O— | | 62.076 |

Example 21 Preparation of 1-Olein-2-Linolein-3-Stearin

*Coix* seed oil solution prepared in tetrahydrofuran (750 mg/mL) was preliminarily separated in CHEETAH-HP100 preparative high performance liquid chromatography (Column: Venusil XBP C18 (2), 50*250 mm, 5 μm, 100 Å; Mobile phase: acetonitrile/tetrahydrofuran=78:22 (v/v); Flow rate of 80 mL/min; Injection volume 2 ml (1.5 g); UV detection wavelength: 205 nm/280 nm). Peak fractions at retention time of 29-38 min were collected, and concentrated under vacuum in nitrogen atmosphere in a rotary evaporator, to give a crude product.

The second purification was proceeded on Venusil XBP C18(L) Column (30*150 mm, 5 μm 150 Å) with acetonitrile:dichloromethane (65/35) as the mobile phase in a flow rate of 32 mL/min. A solution of the above crude product (10 mg/mL) was prepared in dichloromethane, and the injection volume for each separation was 2 mL. UV detection was conducted at 205 nm/280 nm. Peak fraction at retention time of 19 min was collected, and concentrated under vacuum in nitrogen atmosphere in a rotary evaporator. Residues were transferred with chloroform to a 10 mL vial, and dried in a vacuum oven at 35° C. for 6 h. After filling with nitrogen, the dried sample, 1-olein-2-linolein-3-stearin, was frozen in a refrigerator.

HR-EI-MS: m/z=884.7832 (Calcd.=884.7848, C$_{57}$H$_{104}$O$_6$), Degree of unsaturation=6.

IR (KBr film): 1747, 1164, 1098; 2925, 2855, 723; 3008, 1655 cm$^{-1}$ (week).

$^1$H-NMR (CDCl$_3$) data are shown in Table 14.

TABLE 14

$^1$H-NMR spectral data of the compound of Example 21

| Position | Chemical shift | Amount of H, Spike & coupling constant |
|---|---|---|
| H—C═C | 5.35 | 6H, m |
| CH—OCO | 5.26 | 1H, m |
| —CH$_2$—OCO | 4.29 | 2H, dd, 11.4, 4.2 |
| —CH$_2$—OCO | 4.14 | 2H, d, 12.0, 6.0 |
| —CH$_2$COO | 2.32 | 2H, m |
| —CH$_2$COO | 2.30 | 4H, m |
| —CH$_2$—CH═ | 2.03 | 8H, m |
| —CH═CH—CH$_2$—CH═CH— | 2.77 | 2H, t, 6.6 |
| —CH$_2$CH$_2$COO | 1.61 | 6H, m |
| —CH$_2$ | 1.38~1.26 | 64H, m |
| —CH$_3$ | 0.88 | 9H, t, 6.6 |

$^{13}$C-NMR (CDCl$_3$) data are shown in Table 15.

TABLE 15

$^{13}$C-NMR (CDCl$_3$) spectral data of the compound of Example 21

| Position | | Chemical shift |
|---|---|---|
| C1 | 1 | 173.25 |
| | 2 | 172.83 |
| | 3 | 173.25 |
| C2 | 1 | 34.03 |
| | 2 | 34.18 |
| | 3 | 34.04 |
| C3 | 1 | 24.86 |
| | 2$^b$ | 24.86 |
| | 3 | 24.86 |
| C4 | 1 | 29.04~29.76 |
| | 2$^b$ | 29.04~29.76 |
| | 3 | 29.04~29.76 |
| C5 | 1 | 29.04~29.76 |
| | 2$^b$ | 29.04~29.76 |
| | 3 | 29.04~29.76 |
| C6 | 1 | 29.04~29.76 |
| | 2$^b$ | 29.04~29.76 |
| | 3 | 29.04~29.76 |
| C7 | 1 | 29.04~29.76 |
| | 2$^b$ | 29.04~29.76 |
| | 3 | 29.04~29.76 |
| C8 | 1 | 29.04~29.76 |
| | 2 | 27.19 |
| | 3 | 29.04~29.76 |
| C9 | 1 | 129.70 |
| | 2 | 130.01 |
| | 3 | 29.04~29.76 |
| C10 | 1 | 129.97 |
| | 2 | 128.08 |
| | 3 | 29.04~29.76 |
| C11 | 1 | 27.19 |
| | 2 | 25.62 |
| | 3 | 29.04~29.76 |
| C12 | 1 | 29.04~29.76 |
| | 2 | 127.88 |
| | 3 | 29.04~29.76 |
| C13 | 1 | 29.04~29.76 |
| | 2 | 130.22 |
| | 3 | 29.04~29.76 |
| C14 | 1 | 31.89 |
| | 2 | 29.04~29.76 |
| | 3 | 31.89 |
| C15 | 1 | 22.67 |
| | 2$^b$ | 22.56 |
| | 3 | 22.67 |
| C16 | 1 | 31.91 |
| | 2 | 31.52 |
| | 3 | 31.89 |
| C17 | 1 | 22.67 |
| | 2 | 22.56 |
| | 3 | 22.67 |
| C18 | 1 | 14.09 |
| | 2 | 14.05 |
| | 3 | 14.09 |
| CH—O | | 68.89 |
| 2CH$_2$—O | | 62.08 |

Example 22 Preparation of *Coix* Seed Oil Injection of the Invention

Formulation:

| | |
|---|---|
| Coix seed oil | 100 g |
| Soybean lecithin for injection | 10 g |
| Glycerin for injection | 15 g |
| Water for injection added to | 1000 mL | wherein, the *Coix* seed oil contains following ingredients:

| | |
|---|---|
| 1,3-diolein | 0.50% |
| 1-linolein-3-olein | 1.31% |
| 1,2-diolein | 0.30% |
| 1-olein-2-linolein | 0.95% |
| 1,2-dilinolein | 0.41% |
| Trilinolein | 6.10% |
| 1-Olein-2,3-dilinolein | 16.18% |
| 1-Palmitin-2,3-dilinolein | 6.56% |
| 1,3-Diolein-2-linolein | 16.69% |
| 1-Palmitin-2-linolein-3-olein | 12.96% |
| 1,3-Dipalmitin-2-linolein | 2.88% |
| Triolein | 18.30% |
| 1-Palmitin-2,3-diolein | 10.18% |
| 1-olein-2-linolein-3-stearin | 1.72% |
| 1,3-dipalmitin-2-olein | 1.88% |
| 1,2-diolein-3-stearin | 1.60% |

Process:

To a formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection is added to a specified amount, and the mixture was stirred to give a water phase.

A formulated amount of *Coix* seed oil was weighed. The weighed oil and the water phase prepared above were heated separately to 60° C., then mixed and emulsified in a high pressure homogenizer, in which the low pressure was 6 MPa and the high pressure was 30 MPa. The homogenization was repeated for 4 times until the amount of particles below 2 μm was no less than 95% and particles above 5 μm were undetectable. If necessary, NaOH or HCl was used to adjust the pH to 8.5.

The resulting homogeneous emulsion was filtered by nitrogen pressure through a microporous filter of 3 μm or less, then filled under nitrogen, and finally sterilized and cooled to afford the injection.

Example 23 Preparation of *Coix* Seed Oil Injection of the Invention

Formulation:

| | |
|---|---|
| Coix seed oil | 300 g |
| Soybean lecithin acceptable for injection | 40 g |
| Glycerin acceptable for injection | 50 g |
| Water for injection added to | 1000 mL | wherein, the *Coix* seed oil contains following ingredients:

| | |
|---|---|
| 1,3-diolein | 0.40% |
| 1-linolein-3-olein | 1.05% |
| 1,2-diolein | 0.24% |
| 1-olein-2-linolein | 0.76% |
| 1,2-dilinolein | 0.33% |
| Trilinolein | 4.87% |
| 1-Olein-2,3-dilinolein | 17.88% |
| 1-Palmitin-2,3-dilinolein | 5.25% |
| 1,3-Diolein-2-linolein | 15.13% |
| 1-Palmitin-2-linolein-3-olein | 10.26% |
| 1,3-Dipalmitin-2-linolein | 3.05% |
| Triolein | 20.46% |
| 1-Palmitin-2,3-diolein | 11.50% |
| 1-olein-2-linolein-3-stearin | 1.95% |
| 1,3-dipalmitin-2-olein | 2.16% |
| 1,2-diolein-3-stearin | 1.84% |

Process:

To a formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection is added to a specified amount, and the mixture was stirred to give a water phase.

A formulated amount of *Coix* seed oil was weighed. The weighed oil and the water phase prepared above were heated separately to 70° C., then mixed and emulsified in a high pressure homogenizer, in which the low pressure was 12 MPa and the high pressure was 45 MPa. The homogenization was repeated for 3 times until the amount of particles below 2 μm was no less than 95% and particles above 5 μm were undetectable. If necessary, NaOH or HCl was used to adjust the pH to 7.1.

The resulting homogeneous emulsion was filtered by nitrogen pressure through a microporous filter of 3 μm or less, then filled under nitrogen, and finally sterilized and cooled to afford the injection.

Example 24 Preparation of *Coix* Seed Oil Injection of the Invention

Formulation:

| | |
|---|---|
| Coix seed oil | 200 g |
| Soybean lecithin for injection | 25 g |
| Glycerin acceptable for injection | 30 g |
| Water for injection added to | 1000 mL | wherein, the *Coix* seed oil contains following ingredients:

| | |
|---|---|
| 1,3-diolein | 0.45% |
| 1-linolein-3-olein | 1.18% |
| 1,2-diolein | 0.27% |
| 1-olein-2-linolein | 0.86% |
| 1,2-dilinolein | 0.37% |
| Trilinolein | 5.47% |
| 1-Olein-2,3-dilinolein | 18.69% |
| 1-Palmitin-2,3-dilinolein | 6.01% |
| 1,3-Diolein-2-linolein | 18.19% |
| 1-Palmitin-2-linolein-3-olein | 14.11% |
| 1,3-Dipalmitin-2-linolein | 2.60% |
| Triolein | 16.25% |
| 1-Palmitin-2,3-diolein | 9.11% |
| 1-olein-2-linolein-3-stearin | 1.88% |
| 1,3-dipalmitin-2-olein | 2.09% |
| 1,2-diolein-3-stearin | 1.76% |

Process:

To a formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection is added to a specified amount, and the mixture was stirred to give a water phase.

A formulated amount of *Coix* seed oil was weighed. The weighed oil and the water phase prepared above were heated separately to 65° C., then mixed and emulsified in a high pressure homogenizer, in which the low pressure was 10 MPa and the high pressure was 30 MPa. The homogenization was repeated for 5 times until the amount of particles below 2 μm was no less than 95% and particles above 5 μm were undetectable. If necessary, NaOH or HCl was used to adjust the pH to 4.8.

The resulting homogeneous emulsion was filtered by nitrogen pressure through a microporous filter of 3 μm or less, then filled under nitrogen, and finally sterilized and cooled to afford the injection.

Example 25 Preparation of *Coix* Seed Oil Injection of the Invention

Formulation:

| Coix seed oil | 150 g |
|---|---|
| Soybean lecithin acceptable for injection | 35 g |
| Glycerin acceptable for injection | 30 g |
| Water for injection added to | 1000 mL | wherein, the *Coix* seed oil contains following ingredients:

| 1,3-diolein | 0.49% |
|---|---|
| 1-linolein-3-olein | 1.28% |
| 1,2-diolein | 0.29% |
| 1-olein-2-linolein | 0.93% |
| 1,2-dilinolein | 0.40% |
| Trilinolein | 5.96% |
| 1-Olein-2,3-dilinolein | 16.58% |
| 1-Palmitin-2,3-dilinolein | 6.43% |
| 1,3-Diolein-2-linolein | 16.20% |
| 1-Palmitin-2-linolein-3-olein | 12.57% |
| 1,3-Dipalmitin-2-linolein | 2.79% |
| Triolein | 17.69% |
| 1-Palmitin-2,3-diolein | 9.87% |
| 1-olein-2-linolein-3-stearin | 1.75% |
| 1,3-dipalmitin-2-olein | 1.92% |
| 1,2-diolein-3-stearin | 1.66% |

Process:

To a formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection is added to a specified amount, and the mixture was stirred to give a water phase.

A formulated amount of *Coix* seed oil was weighed. The weighed oil and the water phase prepared above were heated separately to 68° C., then mixed and emulsified in a high pressure homogenizer, in which the low pressure was 7 MPa and the high pressure was 35 MPa. The homogenization was repeated for 3 times until the amount of particles below 2 μm was no less than 95% and particles above 5 μm were undetectable. If necessary, NaOH or HCl was used to adjust the pH to 6.8.

The resulting homogeneous emulsion was filtered by nitrogen pressure through a microporous filter of 3 μm or less, then filled under nitrogen, and finally sterilized and cooled to afford the injection.

Example 26 Preparation of *Coix* Seed Oil Capsule of the Invention

Formulation:

| Coix seed oil | 200 g |
|---|---|
| Vitamine E | 0.20 g |
| to give | 1000 capsules | wherein, the *Coix* seed oil contains following ingredients:

| 1,3-diolein | 0.51% |
|---|---|
| 1-linolein-3-olein | 1.34% |
| 1,2-diolein | 0.31% |
| 1-olein-2-linolein | 0.97% |
| 1,2-dilinolein | 0.42% |
| Trilinolein | 6.20% |
| 1-Olein-2,3-dilinolein | 15.93% |
| 1-Palmitin-2,3-dilinolein | 6.69% |
| 1,3-Diolein-2-linolein | 16.87% |
| 1-Palmitin-2-linolein-3-olein | 13.09% |
| 1,3-Dipalmitin-2-linolein | 2.91% |
| Triolein | 18.42% |
| 1-Palmitin-2,3-diolein | 10.27% |
| 1-olein-2-linolein-3-stearin | 1.67% |
| 1,3-dipalmitin-2-olein | 1.86% |
| 1,2-diolein-3-stearin | 1.56% |

Process:

Glue formulation: Gelatin, purified water, glycerin and 10% ethylparaben solution were weighed at a weight ratio of 1:1.2:0.8:0.01. Glycerin, purified water and 10% ethylparaben solution were sequentially added into a glue melting tank and heated to 70° C. Then gelatin was added and constantly stirred under vacuum until the gelatin was completely dissolved. The glue was filtered and stored at 60° C. for use.

Drug liquid formulation: Formulated amount of *Coix* seed oil and vitamin E were added into an ingredient tank and stirred constantly until thoroughly mixed.

Capsule pressing: Proper pellet dies were chosen according to the capsule size. Capsules were pressed under a temperature of 18° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 27 Preparation of *Coix* Seed Oil Capsule of the Invention

Formulation:

| Coix seed oil | 800 g |
|---|---|
| Tween 80 | 0.60 g |
| to give | 1000 capsules | wherein, the *Coix* seed oil contains following ingredients:

| 1,3-diolein | 0.55% |
|---|---|
| 1-linolein-3-olein | 1.44% |
| 1,2-diolein | 0.33% |
| 1-olein-2-linolein | 1.05% |
| 1,2-dilinolein | 0.45% |
| Trilinolein | 6.69% |
| 1-Olein-2,3-dilinolein | 14.75% |
| 1-Palmitin-2,3-dilinolein | 7.21% |
| 1,3-Diolein-2-linolein | 14.92% |
| 1-Palmitin-2-linolein-3-olein | 11.55% |
| 1,3-Dipalmitin-2-linolein | 3.14% |
| Triolein | 19.86% |
| 1-Palmitin-2,3-diolein | 11.08% |

-continued

| | |
|---|---|
| 1-olein-2-linolein-3-stearin | 1.50% |
| 1,3-dipalmitin-2-olein | 1.70% |
| 1,2-diolein-3-stearin | 1.43% |

Process:

Glue formulation: Gelatin, purified water, glycerin and benzoic acid were weighed at a weight ratio of 1:1.2:0.8:0.01. Glycerin, purified water and benzoic acid were sequentially added into a glue melting tank and heated to 90° C. Then gelatin was added and constantly stirred under vacuum until the gelatin was completely dissolved. The glue was filtered and stored at 56° C. for use.

Drug liquid formulation: Formulated amount of *Coix* seed oil and Tween 80 were added into an ingredient tank and stirred constantly until thoroughly mixed.

Capsule pressing: Proper pellet dies were chosen according to the capsule size. Capsules were pressed under a temperature of 26° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 28 Preparation of *Coix* Seed Oil Capsule of the Invention

Formulation:

| | |
|---|---|
| Coix seed oil | 500 g |
| Vitamine E | 0.40 g |
| to give | 1000 capsules | wherein, the *Coix* seed oil contains following ingredients:

| | |
|---|---|
| 1,3-diolein | 0.58% |
| 1-linolein-3-olein | 1.14% |
| 1,2-diolein | 0.35% |
| 1-olein-2-linolein | 0.83% |
| 1,2-dilinolein | 0.47% |
| Trilinolein | 6.99% |
| 1-Olein-2,3-dilinolein | 13.00% |
| 1-Palmitin-2,3-dilinolein | 7.54% |
| 1,3-Diolein-2-linolein | 19.02% |
| 1-Palmitin-2-linolein-3-olein | 14.75% |
| 1,3-Dipalmitin-2-linolein | 3.28% |
| Triolein | 15.96% |
| 1-Palmitin-2,3-diolein | 9.70% |
| 1-olein-2-linolein-3-stearin | 1.38% |
| 1,3-dipalmitin-2-olein | 1.52% |
| 1,2-diolein-3-stearin | 1.29% |

Process:

Glue formulation: Gelatin, purified water, glycerin and potassium sorbate were weighed at a weight ratio of 1:0.9:0.6:0.005. Glycerin, purified water and potassium sorbate were sequentially added into a glue melting tank and heated to 80° C. Then gelatin was added and constantly stirred under vacuum until the gelatin was completely dissolved. The glue was filtered and stored at 62° C. for use.

Drug liquid formulation: Formulated amount of *Coix* seed oil and Vitamin E were added into an ingredient tank and stirred constantly until thoroughly mixed.

Capsule pressing: Proper pellet dies were chosen according to the capsule size. Capsules were pressed under a temperature of 28° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 29 Preparation of *Coix* Seed Oil Capsule of the Invention

Formulation:

| | |
|---|---|
| Coix seed oil | 600 g |
| Tween 80 | 0.3 g |
| to give | 1000 capsules | wherein, the *Coix* seed oil contains following ingredients:

| | |
|---|---|
| 1,3-diolein | 0.45% |
| 1-linolein-3-olein | 1.26% |
| 1,2-diolein | 0.27% |
| 1-olein-2-linolein | 0.88% |
| 1,2-dilinolein | 0.36% |
| Trilinolein | 6.15% |
| 1-Olein-2,3-dilinolein | 18.01% |
| 1-Palmitin-2,3-dilinolein | 6.66% |
| 1,3-Diolein-2-linolein | 16.77% |
| 1-Palmitin-2-linolein-3-olein | 12.89% |
| 1,3-Dipalmitin-2-linolein | 2.88% |
| Triolein | 18.30% |
| 1-Palmitin-2,3-diolein | 8.69% |
| 1-olein-2-linolein-3-stearin | 1.81% |
| 1,3-dipalmitin-2-olein | 2.08% |
| 1,2-diolein-3-stearin | 1.81% |

Process:

Glue formulation: Gelatin, purified water, glycerin and chlorhexidine acetate were weighed at a weight ratio of 1:1.0:0.5:0.008. Glycerin, purified water and chlorhexidine acetate were sequentially added into a glue melting tank and heated to 85° C. Then gelatin was added and constantly stirred under vacuum until the gelatin was completely dissolved. The glue was filtered and stored at 56° C. for use.

Drug liquid formulation: Formulated amount of *Coix* seed oil and Tween 80 were added into an ingredient tank and stirred constantly until thoroughly mixed.

Capsule pressing: Proper pellet dies were chosen according to the capsule size. Capsules were pressed under a temperature of 30° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 30 Preparation of *Coix* Seed Oil Injection of the Invention

Formulation:

| | |
|---|---|
| Coix seed oil | 100 g |
| Soybean lecithin for injection | 10 g |
| Glycerin for injection | 15 g |
| Water for injection added to | 1000 mL | wherein, the *Coix* seed oil contains following ingredients:

| | |
|---|---|
| 1,3-diolein | 0.42% |
| 1-linolein-3-olein | 1.25% |
| 1,2-diolein | 0.25% |
| 1-olein-2-linolein | 0.81% |
| 1,2-dilinolein | 0.35% |
| Trilinolein | 6.85% |
| 1-Olein-2,3-dilinolein | 18.24% |
| 1-Palmitin-2,3-dilinolein | 5.74% |
| 1,3-Diolein-2-linolein | 15.01% |
| 1-Palmitin-2-linolein-3-olein | 10.95% |
| 1,3-Dipalmitin-2-linolein | 2.88% |
| Triolein | 20.75% |
| 1-Palmitin-2,3-diolein | 10.18% |
| 1-olein-2-linolein-3-stearin | 1.92% |
| 1,3-dipalmitin-2-olein | 2.11% |
| 1,2-diolein-3-stearin | 1.84% |

Process:

To a formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection was added to a specified amount, and the mixture was stirred to give a water phase.

A formulated amount of *Coix* seed oil was weighed. The weighed oil and the water phase prepared above were heated separately to 60° C., then mixed and emulsified in a high pressure homogenizer, in which the low pressure was 7 MPa and the high pressure was 26 MPa. The homogenization was repeated for 5 times until the amount of particles below 2 μm was no less than 95% and particles above 5 μm were undetectable. If necessary, NaOH or HCl was used to adjust the pH to 6.8.

The resulting homogeneous emulsion was filtered by nitrogen pressure through a microporous filter of 3 μm or less, then filled under nitrogen, and finally sterilized and cooled to afford the injection.

Example 31 Preparation of *Coix* Seed Oil Injection of the Invention

Formulation:

| | |
|---|---|
| Coix seed oil | 300 g |
| Soybean lecithin acceptable for injection | 40 g |
| Glycerin acceptable for injection | 50 g |
| Water for injection added to | 1000 mL | wherein, the *Coix* seed oil contains following ingredients:

| | |
|---|---|
| 1,3-diolein | 0.46% |
| 1-linolein-3-olein | 1.20% |
| 1,2-diolein | 0.28% |
| 1-olein-2-linolein | 0.90% |
| 1,2-dilinolein | 0.38% |
| Trilinolein | 5.71% |
| 1-Olein-2,3-dilinolein | 15.11% |
| 1-Palmitin-2,3-dilinolein | 6.02% |
| 1,3-Diolein-2-linolein | 16.30% |
| 1-Palmitin-2-linolein-3-olein | 14.20% |
| 1,3-Dipalmitin-2-linolein | 3.20% |
| Triolein | 19.91% |
| 1-Palmitin-2,3-diolein | 9.22% |
| 1-olein-2-linolein-3-stearin | 1.78% |
| 1,3-dipalmitin-2-olein | 2.01% |
| 1,2-diolein-3-stearin | 1.70% |

Process:

To a formulated amount of soybean lecithin acceptable for injection was added an appropriate amount of water for injection. The mixture was dispersed with a high shear dispersing emulsifier into a dispersion without bulks or granules. Formulated amount of glycerin acceptable for injection was added. Then water for injection is added to a specified amount, and the mixture was stirred to give a water phase.

A formulated amount of *Coix* seed oil was weighed. The weighed oil and the water phase prepared above were heated separately to 70° C., then mixed and emulsified in a high pressure homogenizer, in which the low pressure was 11 MPa and the high pressure was 48 MPa. The homogenization was repeated for 6 times until the amount of particles below 2 μm was no less than 95% and particles above 5 μm were undetectable. If necessary, NaOH or HCl was used to adjust the pH to 7.5.

The resulting homogeneous emulsion was filtered by nitrogen pressure through a microporous filter of 3 μm or less, then filled under nitrogen, and finally sterilized and cooled to afford the injection.

Example 32 Preparation of *Coix* Seed Oil Injection of the Invention

Formulation:

| | |
|---|---|
| Coix seed oil | 200 g |
| Soybean lecithin for injection | 25 g |
| Glycerin acceptable for injection | 30 g |
| Water for injection added to | 1000 mL | wherein, the *Coix* seed oil contains following ingredients:

| | |
|---|---|
| 1,3-diolein | 0.50% |
| 1-linolein-3-olein | 1.31% |
| 1,2-diolein | 0.30% |
| 1-olein-2-linolein | 0.95% |
| 1,2-dilinolein | 0.41% |
| Trilinolein | 6.18% |
| 1-Olein-2,3-dilinolein | 17.26% |
| 1-Palmitin-2,3-dilinolein | 6.51% |
| 1,3-Diolein-2-linolein | 15.45% |
| 1-Palmitin-2-linolein-3-olein | 12.83% |
| 1,3-Dipalmitin-2-linolein | 2.81% |
| Triolein | 19.33% |
| 1-Palmitin-2,3-diolein | 9.95% |
| 1-olein-2-linolein-3-stearin | 1.71% |
| 1,3-dipalmitin-2-olein | 1.97% |
| 1,2-diolein-3-stearin | 1.69% |

Process:

To a formulated amount of soybean lecithin for injection was added an appropriate amount of water for injection. The mixture was dispersed with a high shear dispersing emulsifier into a dispersion without bulks or granules. Formulated amount of glycerin acceptable for injection was added. Then water for injection is added to a specified amount, and the mixture was stirred to give a water phase.

A formulated amount of *Coix* seed oil was weighed. The weighed oil and the water phase prepared above were heated separately to 65° C., then mixed and emulsified in a high pressure homogenizer, in which the low pressure was 8 MPa and the high pressure was 40 MPa. The homogenization was repeated for 4 times until the amount of particles below 2 μm was no less than 95% and particles above 5 μm were undetectable. If necessary, NaOH or HCl was used to adjust the pH to 6.5.

The resulting homogeneous emulsion was filtered by nitrogen pressure through a microporous filter of 3 µm or less, then filled under nitrogen, and finally sterilized and cooled to afford the injection.

Example 33 Preparation of *Coix* Seed Oil Capsule of the Invention

Formulation:

| Coix seed oil | 200 g |
|---|---|
| Vitamine E | 0.20 g |
| to give | 1000 capsules | wherein, the *Coix* seed oil contains following ingredients:

| 1,3-diolein | 0.52% |
|---|---|
| 1-linolein-3-olein | 1.40% |
| 1,2-diolein | 0.32% |
| 1-olein-2-linolein | 1.01% |
| 1,2-dilinolein | 0.43% |
| Trilinolein | 6.51% |
| 1-Olein-2,3-dilinolein | 14.09% |
| 1-Palmitin-2,3-dilinolein | 6.84% |
| 1,3-Diolein-2-linolein | 17.65% |
| 1-Palmitin-2-linolein-3-olein | 13.56% |
| 1,3-Dipalmitin-2-linolein | 3.07% |
| Triolein | 18.10% |
| 1-Palmitin-2,3-diolein | 10.80% |
| 1-olein-2-linolein-3-stearin | 1.59% |
| 1,3-dipalmitin-2-olein | 1.73% |
| 1,2-diolein-3-stearin | 1.49% |

Process:

Glue formulation: Gelatin, purified water, glycerin and 10% ethylparaben solution were weighed at a weight ratio of 1:1.2:0.8:0.01. Glycerin, purified water and 10% ethylparaben solution were sequentially added into a glue melting tank and heated to 70° C. Then gelatin was added and constantly stirred under vacuum until the gelatin was completely dissolved. The glue was filtered and stored at 59° C. for use.

Drug liquid formulation: Formulated amount of *Coix* seed oil and Vitamin E were added into an ingredient tank and stirred constantly until thoroughly mixed.

Capsule pressing: Proper pellet dies were chosen according to the capsule size. Capsules were pressed under a temperature of 16° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 34 Preparation of *Coix* Seed Oil Capsule of the Invention

Formulation:

| Coix seed oil | 800 g |
|---|---|
| Tween 80 | 0.60 g |
| to give | 1000 capsules | wherein, the *Coix* seed oil contains following ingredients:

| 1,3-diolein | 0.56% |
|---|---|
| 1-linolein-3-olein | 1.11% |
| 1,2-diolein | 0.34% |
| 1-olein-2-linolein | 0.91% |
| 1,2-dilinolein | 0.46% |
| Trilinolein | 6.71% |
| 1-Olein-2,3-dilinolein | 16.31% |
| 1-Palmitin-2,3-dilinolein | 7.25% |
| 1,3-Diolein-2-linolein | 18.50% |
| 1-Palmitin-2-linolein-3-olein | 11.90% |
| 1,3-Dipalmitin-2-linolein | 2.63% |
| Triolein | 17.14% |
| 1-Palmitin-2,3-diolein | 11.21% |
| 1-olein-2-linolein-3-stearin | 1.42% |
| 1,3-dipalmitin-2-olein | 1.60% |
| 1,2-diolein-3-stearin | 1.31% |

Process:

Glue formulation: Gelatin, purified water, glycerin and benzoic acid were weighed at a weight ratio of 1:1.2:0.8:0.01. Glycerin, purified water and benzoic acid were sequentially added into a glue melting tank and heated to 90° C. Then gelatin was added and constantly stirred under vacuum until the gelatin was completely dissolved. The glue was filtered and stored at 60° C. for use.

Drug liquid formulation: Formulated amount of *Coix* seed oil and Tween 80 were added into an ingredient tank and stirred constantly until thoroughly mixed.

Capsule pressing: Proper pellet dies were chosen according to the capsule size. Capsules were pressed under a temperature of 26° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 35 Preparation of *Coix* Seed Oil Capsule of the Invention

Formulation:

| Coix seed oil | 500 g |
|---|---|
| Vitamine E | 0.40 g |
| to give | 1000 capsules | wherein, the *Coix* seed oil contains following ingredients:

| 1,3-diolein | 0.57% |
|---|---|
| 1-linolein-3-olein | 1.21% |
| 1,2-diolein | 0.34% |
| 1-olein-2-linolein | 0.86% |
| 1,2-dilinolein | 0.46% |
| Trilinolein | 5.13% |
| 1-Olein-2,3-dilinolein | 16.03% |
| 1-Palmitin-2,3-dilinolein | 7.25% |
| 1,3-Diolein-2-linolein | 18.61% |
| 1-Palmitin-2-linolein-3-olein | 12.03% |
| 1,3-Dipalmitin-2-linolein | 3.01% |
| Triolein | 18.60% |
| 1-Palmitin-2,3-diolein | 11.21% |
| 1-olein-2-linolein-3-stearin | 1.39% |
| 1,3-dipalmitin-2-olein | 1.53% |
| 1,2-diolein-3-stearin | 1.30% |

Process:

Glue formulation: Gelatin, purified water, glycerin and potassium sorbate were weighed at a weight ratio of 1:0.9:0.6:0.005. Glycerin, purified water and potassium sorbate were sequentially added into a glue melting tank and heated to 80° C. Then gelatin was added and constantly stirred under vacuum until the gelatin was completely dissolved. The glue was filtered and stored at 62° C. for use.

Drug liquid formulation: Formulated amount of *Coix* seed oil and Vitamin E were added into an ingredient tank and stirred constantly until thoroughly mixed.

Capsule pressing: Proper pellet dies were chosen according to the capsule size. Capsules were pressed under a temperature of 20° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

What is claimed is:

1. A *Coix* seed oil, comprising 5 diglyceride and 11 triglyceride ingredients in the following mass percentages: 1,3-diolein 0.40-0.58%, 1-linolein-3-olein 0.91-1.31%, 1,2-diolein 0.24-0.35%, 1-olein-2-linolein 0.66-0.95%, 1,2-dilinolein 0.33-0.47%, trilinolein 4.87-6.99%, 1-olein-2,3-dilinolein 13.00-18.69%, 1-palmitin-2,3-dilinolein 5.25-7.54%, 1,3-diolein-2-linolein 13.23-19.02%, 1-palmitin-2-linolein-3-olein 10.26-14.75%, 1,3-dipalmitin-2-linolein 2.28-3.28%, triolein 14.44-20.76%, 1-palmitin-2,3-diolein 8.06-11.58%, 1-olein-2-linolein-3-stearin 1.37-1.97%, 1,3-dipalmitin-2-olein 1.52-2.19% and 1,2-diolein-3-stearin 1.29-1.86%.

2. The *Coix* seed oil of claim 1, having the following physicochemical constants based on the fatty oil detection specific gravity at 20° C. 0.916-0.920, refractive index at 20° C. 1.471-1.474, acid value <0.2, iodine value 100-106, saponification value 186-195; wherein said diglyceride and triglyceride ingredients are in the following mass percentages: 1,3-diolein 0.45-0.55%, 1-linolein-3-olein 1.03-1.25%, 1,2-diolein 0.27-0.33%, 1-olein-2-linolein 0.75-0.91%, 1,2-dilinolein 0.37-0.45%, trilinolein 5.47-6.69%, 1-olein-2,3-dilinolein 14.63-17.88%, 1-palmitin-2,3-dilinolein 5.90-7.21%, 1,3-diolein-2-linolein 14.88-18.19%, 1-palmitin-2-linolein-3-olein 11.55-14.11%, 1,3-dipalmitin-2-linolein 2.57-3.14%, triolein 16.25-19.86% 1-palmitin-2,3-diolein 9.07-11.08%, 1-olein-2-linolein-3-stearin 1.54-1.88%, 1,3-dipalmitin-2-olein 1.71-2.09% and 1,2-diolein-3-stearin 1.45-1.78%.

3. The *Coix* seed oil of claim 2, wherein said diglyceride and triglyceride ingredients are in the following mass percentages: 1,3-diolein 0.49-0.51%, 1-linolein-3-olein 1.12-1.16%, 1,2-diolein 0.29-0.31%, 1-olein-2-linolein 0.81-0.85%, 1,2-dilinolein 0.40-0.42%, trilinolein 5.96-6.20%, 1-olein-2,3-dilinolein 15.93-16.58%, 1-palmitin-2,3-dilinolein 6.43-6.69%, 1,3-diolein-2-linolein 16.20-16.87%, 1-palmitin-2-linolein-3-olein 12.57-13.09%, 1,3-dipalmitin-2-linolein 2.79-2.91%, triolein 17.69-18.42%, 1-palmitin-2,3-diolein 9.87-10.27%, 1-olein-2-linolein-3-stearin 1.68-1.74%, 1,3-dipalmitin-2-olein 1.86-1.94% and 1,2-diolein-3-stearin 1.58-1.65%.

4. The *Coix* seed oil of claim 1, obtained by a process comprising steps of:

(1) Supercritical carbon dioxide extraction:

Crushing *Coix* seeds into 20-100 mesh powder and extracting the powder using a supercritical $CO_2$ extraction system in which *Coix* seed powder is put in 600 L×2 extractors; the $CO_2$ preheater, extractor and separation column are heated by jacketed circulating hot water to make the extraction temperature and separation temperature to be 33-45° C. and 30-45° C., respectively; the outlet temperatures of separator I and separator II are kept at 20-50° C. and 15-35° C., respectively; the liquid $CO_2$ is pressed at a flow rate of 1-3t/h into the $CO_2$ preheater via a high pressure pump, turning into a fluid in supercritical state; in the extractor, an oil is extracted into the $CO_2$ fluid at a pressure of 19-23 Mpa; then the $CO_2$ fluid with this oil enters the separation column in which the pressure is controlled to 7-10 Mpa to separate this oil; the $CO_2$ gas out from the separation column enters sequentially into separator I and separator II in which the pressure is sustained at 5-7 Mpa and 4-6 Mpa, respectively; impurities such as water separated therefrom are discarded; the $CO_2$ gas returns to liquid $CO_2$ for reuse through a condenser; and a continuous extraction for 2-3 h affords a crude *Coix* seed oil; and (2) Refining process comprises steps of:

adding petroleum ether (bp. 60° C.-90° C.) into the crude *Coix* seed oil obtained by the supercritical $CO_2$ extraction in an amount of 65% of the oil weight; adding 2% NaOH aqueous solution in an amount ranging from 36% to 56% of the oil weight according to the acid value; after stirring the mixture for 10 min and standing for 18-24 h, removing the lower niger layer; washing the upper layer with purified water and letting stand for 18-24 h; after the removal of the lower waste water, washing the upper layer again; after another standing for 40-50 h, removing the lower waste water; and demulsifying the upper layer with acetone in an amount of 70%-90% of the oil weight; after standing for 2-4 h, removing the lower waste acetone and adding 3% to 8% of activated neutral alumina by weight of crude oil in the upper oil layer; stirring the mixture for 30 min, then filtering off the precipitation; heating the filtrate and adding 2% to 6% of activated mixed adsorbent by weight of crude oil; stirring the mixture for 30 min at 40-50° C. and then filtering off the precipitation; concentrating the filtrate under a reduced pressure to recover the solvent, then washing again with purified water; after standing for 1-2 h, removing the lower waste water and heating the upper oil layer and vacuum concentrating it under nitrogen atmosphere; then sterilizing the oil via dry heat sterilization under vacuum at 160-170° C. for 1-2 h; after cooling, filtering the oil through a 0.2 μm microporous membrane; then split charging the obtained *Coix* seed oil in 500 mL glass infusion bottles, nitrogenizing and sealing the bottles.

5. The *Coix* seed oil of claim 4, wherein said refining process comprises steps of:

adding petroleum ether (bp. 60° C.-90° C.) into the *Coix* seed oil obtained by the supercritical $CO_2$ extraction in an amount of 65% of the oil weight; adding 2% NaOH aqueous solution in an amount ranging from 36% to 56% of the oil weight according to the acid value; after stirring the mixture for 10 min and standing for 20 h, removing the lower niger layer; washing the upper layer with purified water and letting standing for 22 h; after the removal of the lower waste water, washing the upper layer again; after standing for another 46 h, removing the lower waste water; demulsifying the upper layer with acetone in an amount of 70%-90% by weight of the crude oil and standing for 3 h; removing the lower waste acetone and adding 5% of activated neutral alumina by weight of crude oil in the upper oil layer; stirring the mixture for 30 min, then filtering off the precipitation; heating the filtrate, and adding 4% of mixed adsorbent of activated kaolin and activated carbon (1:1); stirring the mixture for 30 min at 40-50° C., and then filtering off the precipitation; concentrating the filtrate under a reduced pressure to recover the solvent, then washing again with purified water; after standing for 1 h, removing the lower waste water; heating the upper oil layer and vacuum concentrating it in nitrogen atmosphere; then sterilizing the concentrated oil via dry heat sterilization under vacuum at 160-170° C. for 2 h; after cooling, filtering the oil through a 0.2 μm microporous membrane; then split charging the obtained *Coix* seed oil in 500 mL glass infusion bottles, nitrogenizing and sealing the bottles.

6. The *Coix* seed oil of claim 1, for use in the preparation of antitumor drugs for treatment of tumors selecting from a group consisting of lung cancer, liver cancer, pancreatic cancer, prostate cancer, ovarian cancer and breast cancer, in early, middle or late stage.

* * * * *